United States Patent [19]

Kubokawa et al.

[11] Patent Number: 4,960,106
[45] Date of Patent: Oct. 2, 1990

[54] ENDOSCOPE APPARATUS

[75] Inventors: Hiroaki Kubokawa; Takashi Tsukaya, both of Hachioji; Yasuhiro Ueda, Kokubunji; Takeaki Nakamura, Hino; Yutaka Ohshima, Hachioji; Hiroki Hibino, Hachioji; Shyuichi Takayama, Hachioji; Tadao Hagino, Yokohama, all of Japan

[73] Assignee: Olympus Optical Co., Ltd., Tokyo, Japan

[21] Appl. No.: 186,852

[22] Filed: Apr. 27, 1988

[30] Foreign Application Priority Data

| Apr. 28, 1987 | [JP] | Japan | 62-105869 |
| Jul. 8, 1987 | [JP] | Japan | 62-171942 |
| Jul. 15, 1987 | [JP] | Japan | 62-176532 |
| Aug. 10, 1987 | [JP] | Japan | 62-199396 |
| Aug. 10, 1987 | [JP] | Japan | 62-199395 |
| Aug. 10, 1987 | [JP] | Japan | 62-199393 |
| Aug. 11, 1987 | [JP] | Japan | 62-200292 |
| Aug. 18, 1987 | [JP] | Japan | 62-205539 |
| Aug. 18, 1987 | [JP] | Japan | 62-205540 |

[51] Int. Cl.⁵ .................. A61B 1/00; A61B 5/055
[52] U.S. Cl. .......................... 128/6; 128/4; 128/653 SC
[58] Field of Search .......... 128/6, 653, 4, 654, 128/656, 658

[56] References Cited

U.S. PATENT DOCUMENTS

| 4,433,692 | 2/1984 | Baba | 128/6 |
| 4,489,727 | 12/1984 | Matsuo et al. | 128/6 |
| 4,572,198 | 2/1986 | Codrington | 128/658 |
| 4,616,631 | 10/1986 | Takahashi | 128/6 |
| 4,672,972 | 6/1987 | Berke | 128/653 |
| 4,681,093 | 7/1987 | Ono et al. | 128/6 |
| 4,737,142 | 4/1988 | Heckele | 128/6 |

FOREIGN PATENT DOCUMENTS 59-88140  5/1984  Japan .
62-500048 1/1987  Japan .

Primary Examiner—Edward M. Coven
Assistant Examiner—Jessica J. Harrison
Attorney, Agent, or Firm—Armstrong, Nikaido, Marmelstein, Kubovcik & Murray

[57] ABSTRACT

This NMR metering endoscope apparatus is provided with an endoscope body and an NMR metering loop-like antenna. The endoscope body is provided with an elongate insertable part having an observing window and illuminating window in the tip part an observing system for observing an object by receiving a light coming from the object and entering through the observing window and an illuminating light outputting system emitting an illuminating light out of the illuminating window. The NMR metering antenna is fitted to the outer periphery including the tip surface of the insertable part of the endoscope body and can be connected to the NMR metering apparatus.

23 Claims, 25 Drawing Sheets

FIG. 27(A)    FIG. 27(B)
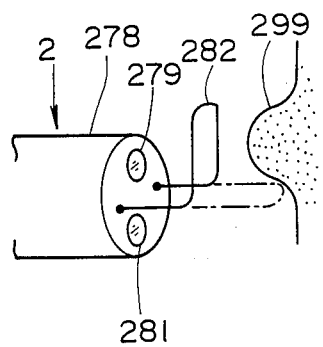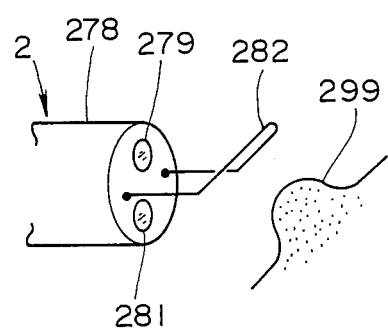
FIG. 28(A)    FIG. 28(B)
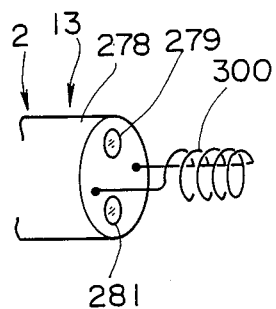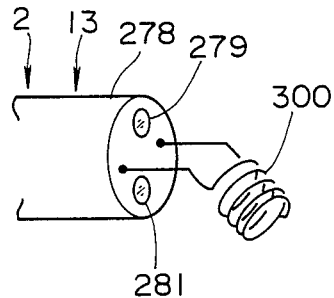

ENDOSCOPE APPARATUS

BACKGROUND OF THE INVENTION

1. Field of the Invention

This invention relates to an endoscope apparatus whereby NMR (nuclear magnetic resonance) can be metered from within a body by leading an antenna into the body through an endoscope.

2. Related Art Statement

Conventionally, in detecting and diagnosing a cuticle cancer or the like generated on the inner surface of a digestive organ of a human body or particularly in the upper layer part of a stomach wall, there has been a general method wherein the generating position is detected with an endoscope or X-ray photographing and the living body tissue of such position is collected and is diagnosed to be bad or not. However, in such conventional method, there have been problems that the sample collecting position is in an area so comparatively wide that the diagnosis can not be immediately made, that the effort of collecting the living body tissue is very large and that the human body is damaged.

On the other hand, against it, recently, there has come to be developed a non-attacking human body diagnosing method utilizing a nuclear magnetic resonance (abbreviated as NMR hereinafter) phenomenon. For example, in an NMR imaging apparatus utilizing the above mentioned NMR phenomenon, a human body is placed in a magnetic field, a high frequency (magnetic field) of a predetermined frequency is given to the human body, a nucleus having a spin within the human body is excited and an NMR signal of a predetermined frequency from this excited nucleus is sensed and is processed with a computer to obtain a sectioned image. The sectioned image obtained by this NMR imaging apparatus is very useful for diagnosing a cancer or the like. That is to say, generally, the NMR signals obtained from a cancer cell and normal cell are known to be different in the relieving time. The diagnosis of whether it is a cancer or not is made possible by measuring this relieving time.

However, in the above mentioned NMR imaging apparatus, in order to obtain a sectioned image, enormous NMR signals must be processed, a high speed large capacity computer is required and the entire apparatus becomes large and expensive.

Conventionally, at the time of the endoscope observation, in case a visually abnormal part is discovered, whether this abnormal part is, for example, bad or not, will be desired to be judged to some extent. However, for such desire, there are problems that the above mentioned NMR imaging apparatus is expensive and large and that further it is difficult to make the part recognized to be visually abnormal and the sectioned image correspond to each other.

In order to cope with it, as show, for example, in the gazettes of a Japanese patent applications laid open Nos. 88140/1984 and a Japanese patent application publication No. 500048/1987 (international laid open No. @086/01093), there is suggested an NMR endoscope wherein, in the tip part of an endoscope insertable part, a high frequency magnetic field is formed and a high frequency coil detecting NMR signals is provided. According to this NMR endoscope, when the above mentioned high frequency coil is pressed against an abnormal position and the NMR signal of the abnormal position is detected, the physiological variation of this abnormal position, for example, whether it is a cancer or not can be detected and diagnosed.

However, in the conventional NMR endoscope, there is a problem that, as the high frequency coil is contained within the tip part body of the endoscope, the tip part becomes so large that the pain given to the patient will be great.

In case a diseased part within a body cavity is to be NMR metered through an endoscope, unless the antenna is pressed against an object position, for example, for several tens of seconds to several minutes, no accurate metering will be able to be made. However, in an endoscope containing an antenna in the tip part, it has been difficult to fix the above mentioned antenna in an object position.

Now, there is a case that an antenna is inserted into a body cavity through an endoscope to meter NMR from within the body and such NMR apparatus as an NMR imaging apparatus is used simultaneously to observe NMR from without the body. However, as the antenna to be inserted into the body cavity is conventionally made of a metal, when the NMR image from without the body is to be observed with this antenna as inserted within the body cavity, the magnetic field of the NMR apparatus for observing from without the body will be disturbed and no good picture image will be obtained. Therefor, in case the NMR image from without the body is to be observed, it will be necessary to pull out the endoscope and the operation will be complicated.

In the above mentioned antenna, it is desirable to make the detecting direction coincide with the direction of the high frequency magnetic field made by this antenna itself. However, in the conventional NMR endoscope, as the antenna is fixed to the tip part, it has been difficult to make the detecting direction coincide with the high frequency magnetic field.

OBJECT AND SUMMARY OF THE INVENTION

An object of the present invention is to provide an endoscope apparatus wherein an NMR metering antenna can be provided without enlarging the outside diameter of the insertable part.

Another object of the present invention is to provide an endoscope apparatus wherein an NMR metering antenna can be easily fixed in an object position.

Further another object of the present invention is to provide an endoscope apparatus wherein the direction of the high frequency magnetic field generated by an NMR metering antenna and the detecting direction can be easily made to coincide with each other.

The NMR metering endoscope apparatus of the present invention is provided with an endoscope body and an NMR metering loop-like antenna. The above mentioned endoscope body is provided with an elongate insertable part having an observing window and illuminating window in the tip part, an observing means for observing an object by receiving a light coming from the object and entering through the above mentioned observing window and an illuminating light outputting means emitting an illuminating light out of the above mentioned illuminating window. The above mentioned NMR metering antenna is fitted to the outer periphery including the tip surface of the insertable part of the above mentioned endoscope body and can be connected to the NMR metering apparatus.

The other features and advantages of the present invention will become apparent enough with the following explanation.

BRIEF DESCRIPTION OF THE DRAWINGS

FIG. 1 is a sectioned view of the tip part of the insertable part of an endoscope.

FIG. 2 is an explanatory view of an endoscope apparatus as being used.

FIG. 3 is a perspective view of the tip part as a hood is removed.

FIG. 4 is a perspective view showing the hood.

FIG. 5 is a circuit diagram showing an NMR metering means.

FIG. 11 is a sectioned view of the tip part of the insertable part of an endoscope.

FIG. 12 is an explanatory view of an endoscope apparatus as being used.

FIG. 13 is a perspective view of the tip part of the insertable part of an endoscope.

FIG. 14 is an explanatory view showing an endoscope apparatus.

FIG. 15 is an explanatory view showing an essential part of the endoscope.

FIG. 16 is a circuit diagram showing an NMR metering means.

FIG. 17 is an explanatory view showing a pipe line when used as an antenna.

FIG. 18 is an explanatory view showing the pipe line when not used as an antenna.

FIG. 19 is a perspective view showing the tip part of the insertable part of an endoscope when metering NMR.

FIG. 20 is a sectioned view of the tip part of the insertable part of the endoscope.

FIG. 21 is an explanatory view showing an endoscope apparatus.

FIG. 22 is a perspective view of the tip part of the insertable part as a balloon is contracted.

FIG. 23 is a perspective view of the tip part of the insertable part as the balloon is inflated.

FIG. 24 is a perspective view of the tip part of the insertable part as the balloon is contracted.

FIG. 25 is a perspective view of the tip part of the insertable part as the balloon is inflated.

FIGS. 26 and 27 relate to the fifth embodiment of the present invention.

FIG. 26 is an explanatory view showing the formation of an endoscope.

FIG. 27(A) is an explanatory view of the tip part of the insertable part as an antenna is bent at right angles.

FIG. 27(B) is an explanatory view of the tip part of the insertable part as the antenna is bent at a predetermined angle.

FIG. 28 relates to a modification of the fifth embodiment.

FIG. 28(A) is an explanatory view showing an antenna before the modification.

FIG. 28(B) is an explanatory view showing the antenna after the modification.

FIG. 29 is a perspective view showing an entire endoscope apparatus.

FIG. 30 is a sectioned view of the tip part of the insertable part of an endoscope.

FIG. 31 is an explanatory view showing an NMR metering means.

FIG. 34 is an explanatory view showing the formation of an endoscope apparatus.

FIG. 35 is a sectioned view of an angle wire.

FIG. 46 is a perspective view showing the insertable part of an endoscope.

FIG. 47 is a sectioned view of the insertable part of the endoscope.

FIG. 48 is a sectioned view showing the vicinity of an antenna.

FIG. 51 is a perspective view showing the insertable part of an endoscope.

FIG. 52 is a sectioned view of the insertable part of the endoscope.

DETAILED DESCRIPTION OF THE PREFERRED EMBODIMENT

FIGS. 1 to 5 show the first embodiment of the present invention.

Figure 2:
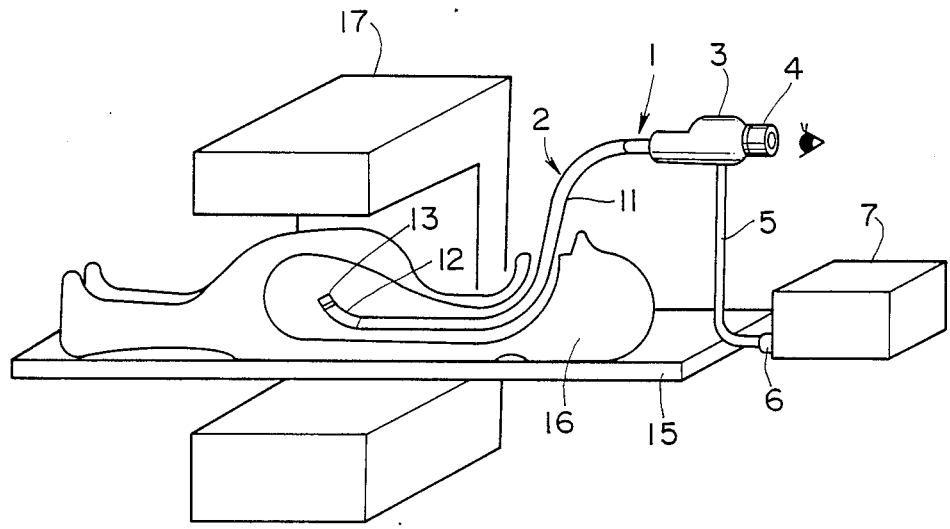

As shown in FIG. 2, an NMR endoscope 1 is provided with an elongate, for example, flexible insertable part 2 to the rear end of which a thick operating part 3 is connected. An eyepiece part 4 is connected to the rear end of the above mentioned operating part 3. A flexible universal cord 5 is extended sidewise from the rear end part of the above mentioned operating part 3. A connector 6 is provided at the tip of this universal cord 5. The NMR endoscope 1 is to be connected to a light source apparatus 7 containing, for example, an NMR metering apparatus.

The above mentioned insertable part 2 is formed of a flexible part 11 provided on an operating part 3 side, a curvable part 12 connected to the tip of this flexible part 11 and a tip part 13 connected to the tip of this curvable part 12. The above mentioned curvable part 12 can be curved vertically and horizontally by rotating and operating a curving operation knob not illustrated provided on the above mentioned operating part 3.

In the case of metering NMR, as shown in FIG. 2, the above mentioned NMR endoscope 1 will be used as combined with an NMR apparatus 17 arranged to enclose an examinee 16 mounted on a bed 15. This NMR apparatus 17 is provided with such means for generating a static magnetic field as a permanent magnet, paraconductive magnet or superconductive magnet.

Figure 1:
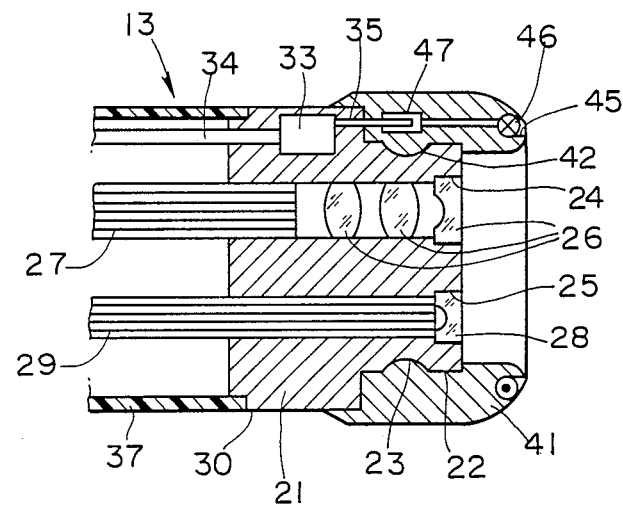
FIGS. 1 to 5 relate to the first embodiment of the present invention.

The above mentioned tip part 13 is formed as shown in FIG. 1.

Figure 3:
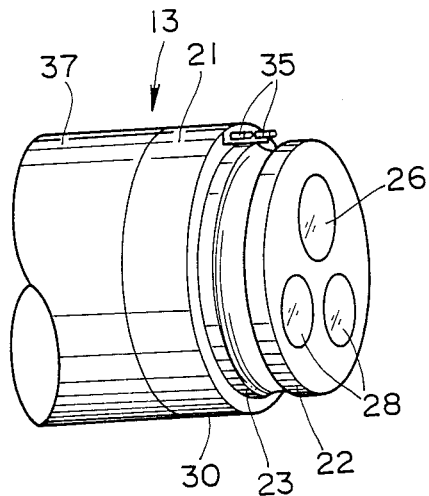

That is to say, the tip part 13 is provided with a tip part body 21 made of such rigid material as a metal and formed to be substantially columnar and to be small in the diameter on the tip side as shown in FIG. 3. An engaging part 23 consisting of a peripheral recess is formed in the body 21. An observing through hole 24 and illuminating through hole 25 passing parallelly in the axial direction through the insertable part 2 are formed in the above mentioned tip part body 21. The above mentioned observing through hole 24 is fitted with an objective lens system 26 on the tip side. The tip surface of an image guide 27 made of a fiber bundle and inserted through the above mentioned insertable part 2 is arranged in the image forming position of this objective lens system 26. An object image formed by the above mentioned objective lens system 26 will be led to the above mentioned eyepiece part 4 through the above mentioned image guide of fibers 27 so as to be able to be observed from this eyepiece part 4. The above mentioned illuminating through hole 25 is fitted with a light distributing lens 28 on the tip side. A light guide 29 made of a fiber bundle is arranged on the rear end side of this light distributing lens 28, is inserted through the above mentioned insertable part 2 and universal cord 5 and is connected to the above mentioned connector 6. When this connector 6 is connected to the above mentioned light source apparatus 7, an illuminating light will be able to be fed to the entrance and of the light guide 29.

A condenser box 33 is arranged on the outer peripheral side within the large diameter part 30 on the rear end side of the above mentioned tip part body 21. Such signal cable 34 as a coaxial cable is connected to the rear end of this condenser box 33, is inserted through the above mentioned insertable part 2 and universal cord 5 and is connected to the above mentioned connector 6. For example, two connector pins 35 are provided to project on the tip side of the above mentioned condenser box 33 and project toward the tip side out of a step between the large diameter part 30 and small diameter part 22 of the above mentioned tip part body 21 as shown in FIG. 3.

A flexible tube 37 forming a jacket tube of the insertable part 2 is connected to the rear end part of the above mentioned tip part body 21 and contains the above mentioned image guide 27, light guide 29 and signal cable 34.

Figure 4:
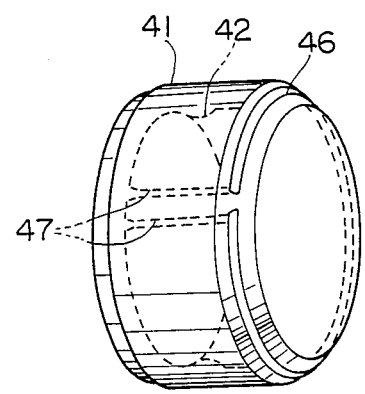

Now, in this embodiment, a hood 41 for protecting, for example, the above mentioned objective lens system 26 and light distributing lens 28 is removably provided on the tip side of the above mentioned tip part body 21, is formed to be substantially like a thick walled cylinder of an outside diameter substantially the same as or somewhat larger than of the above mentioned tip part body 21 as shown in FIG. 4 and has an engaging part 42 consisting of a peripheral projection engaging with the engaging part 23 provided on the above mentioned tip part body 21 formed on the rear end side of the inner peripheral part. When the above mentioned hood 41 is externally fitted to the tip side of the above mentioned tip part body 21 and the engaging parts 23 and 42 are engaged with each other, the above mentioned hood 41 will be fixed to the above mentioned tip part body 21. When fixed to the above mentioned tip part body 21, the above mentioned hood 41 will project at the tip forward of the tip surface of the above mentioned tip part body 21. In this embodiment, a peripheral groove 45 opening on the tip side is formed on the tip part of the above mentioned hood 41 and contains an NMR metering antenna (coil) 46 so as to be exposed. This antenna 46 is formed to be like a single winding loop, is bent at both ends to the rear end side and is connected to two connector receptacles 47 provided in the positions corresponding to connector pins 35 projecting out of the above mentioned tip part body 21.

Figure 5:
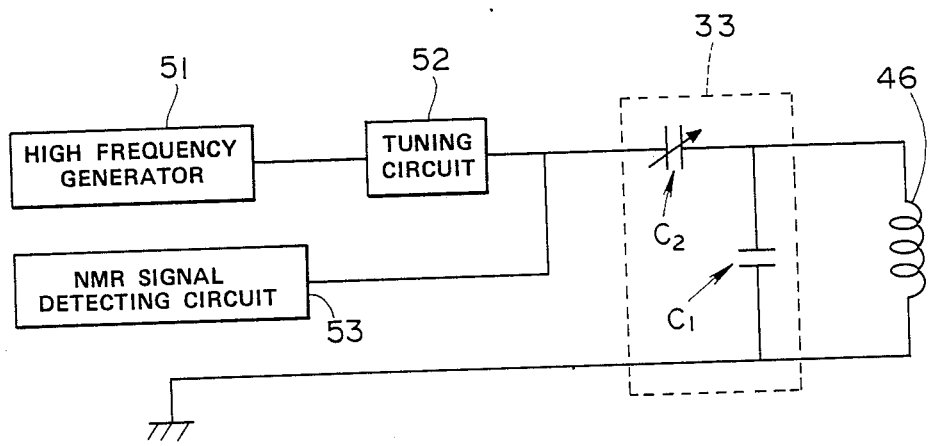

The NMR metering means including the above mentioned antenna 46 is formed as shown, for example, in FIG. 5.

The condenser box 33 within the tip part body 21 is connected to the above mentioned antenna 46 through the above mentioned connector receptacles 47 and connector pins 35. For example, a high frequency generated from a high frequency generator 51 provided within the above mentioned light source apparatus 7 and tuned to a resonance frequency corresponding to a metering object nucleus kind by a tuning circuit will be delivered to the above mentioned antenna 46 through the above mentioned condenser box 33 and a high frequency magnetic field will be delivered to a living body from this antenna 46. By the way, in this embodiment, the direction of the above mentioned high frequency magnetic field, that is, the detecting direction will be parallel with the axial direction of the insertable part 2. A condenser $C_1$ in parallel with the above mentioned antenna 46 and a variable condenser $C_2$ in series with the above mentioned antenna 46 are contained within the above mentioned condenser box 33. A matching circuit matching the impedances on the above mentioned antenna 46 side and high frequency generator 51 side is formed of these condensers $C_1$ and $C_2$.

In this embodiment, the above mentioned antenna 46 is to transmit and receive signals. An NMR signal from a living body will be received by the above mentioned antenna 46 and will be input into an NMR signal detecting circuit 53 through the above mentioned condenser box 33. Such information (NMR parameter) as the relieving time ($T_1$, $T_2$) will be obtained in this NMR signal detecting circuit 53.

The operation of this embodiment formed as in the above shall be explained in the following.

As shown in FIG. 2, the examinee 16 is mounted on the bed 15 and a static magnetic field is given to the examinee 16 by the NMR apparatus 17. In this state, the insertable part 2 of the NMR endoscope 1 is inserted through the mouth cavity or the like of the examinee 16, an illuminating light is fed to the light guide 29 of the NMR endoscope 1 and a stomach wall upper layer part or the like is observed with the observing optical system consisting of the objective lens system 26, image guide 27 and eyepiece part 4. For example, in case an abnormal position is discovered in the stomach wall upper layer part, a curving operation knob or the like of the operating part 3 is operated to press the antenna 46 provided in the hood 41 on the tip side of the tip part 13 against the abnormal position. In this state, a high frequency will be delivered to the above mentioned antenna 46 through the high frequency generator 51, tuning circuit 52 and condenser box 33 and a high frequency magnetic field will be delivered to the abnormal position from this antenna 46. By the way, it is desirable that the direction of this high frequency magnetic field intersects at right angles with the direction of the magnetic field. When the NMR signal from the abnormal position is received by the above mentioned antenna 46 and is metered by the NMR signal detecting circuit 53, the physiological variation of the abnormal position, for example, whether it is a cancer or not will be able to be detected.

In this embodiment, the NMR metering antenna 46 is provided in the hood 41 of the tip part 13. Therefore, the antenna 46 can be provided in the tip part 13 at a high space efficiency and the tip part 13 can be made smaller in the size and diameter than in the case that the antenna 46 is contained within the tip part 13.

Further, the antenna 46 can be formed to be like a loop having substantially the same diameter as the outside diameter of the tip part 13. FIGS. 6 to 10 show a modification of the first embodiment.

Figure 6:
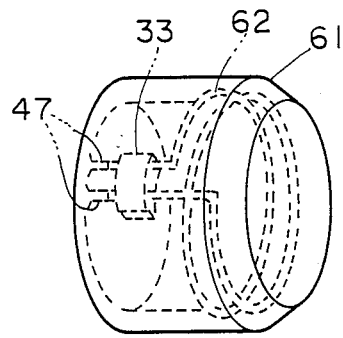
FIG. 6 is a perspective view of the hood in the first modification of the first embodiment.

In the first modification shown in FIG. 6, a condenser box 33 connected to connector receptacles 47 is provided within a thick-walled substantially cylindrical hood 61 and is connected with an NMR metering antenna 62. This antenna 62 is embedded in the above mentioned hood 61 and is wound several times, for example, twice in the peripheral direction.

The other formations are the same as in the first embodiment.

According to this modification, as the condenser box 33 is provided within the hood 61, the tip part body 21 can be made smaller in the size and diameter.

Figure 7:
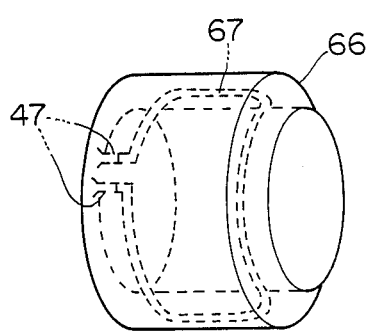
FIG. 7 is a perspective view of the hood in the second modification of the first embodiment.

In the second modification shown in FIG. 7, a saddle-like antenna 67 is embedded on one side of the diametral direction within a substantially cylindrical hood 66. The other formation are the same as in the first embodiment.

In this modification, the direction of the high frequency magnetic field delivered from the above mentioned antenna 67, that is, the detecting direction is a direction intersecting at right angles with the axial direction of the insertable part 2 and NMR can be metered by contacting the side part of the above mentioned hood 66 with the part to be examined. Also, the detecting direction can be changed in response to the examined part by replacing the hood 66 of this modification with the hood 46 of the first embodiment.

Figure 8:
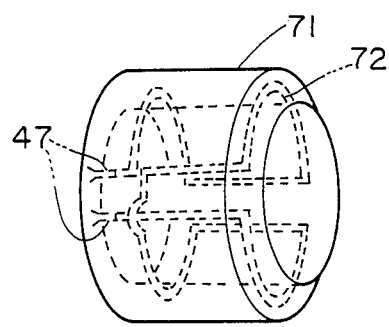
FIG. 8 is a perspective view of the hood in the third modification of the first embodiment.

In the third modification shown in FIG. 8, an antenna 72 is wound to be like saddles on both sides of the diametral direction within a substantially cylindrical hood 71. The other formations are the same as in the first embodiment.

According to this modification, the same as in the second modification, the detecting direction is a direction intersecting at right angles with the axial direction of the insertable part 2 and the magnetic field can be made large.

Figure 9:
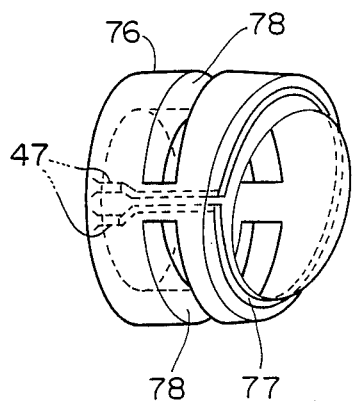
FIG. 9 is a perspective view of the hood in the fourth modification of the first embodiment.

In the fourth modification shown in FIG. 9, a substantially cylindrical hood 76 is formed at the tip to be oblique to the axial direction of the insertable part 2, has a peripheral groove formed at the tip and contains an antenna 77 in this groove. The above mentioned hood 76 is provided with two semicircular incisions 78 in symmetrical positions in the direction vertical to the axial direction so as to be somewhat rotatable on the tip side.

According to this modification, the above mentioned antenna 77 provided on the rotatable tip side of the hood 76 can be positively closely contacted with the part to be examined.

Figure 10:
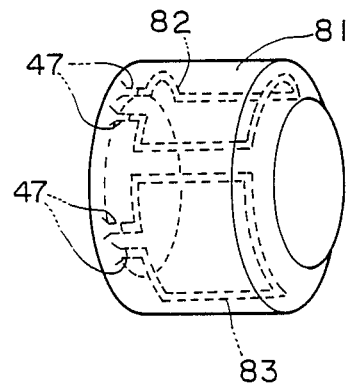
FIG. 10 is a perspective view of the hood in the fifth modification of the first embodiment.

In the fifth modification shown in FIG. 10, a plurality of, for example, two saddle-like antennae 82 and 83 are embedded in the peripheral direction within a substantially cylindrical hood 81 and are connected respectively to connector receptacles 47.

According to this embodiment, for example, when the detecting directions by the above mentioned antennae 82 and 83 are made different from each other, the detecting direction will be able to be changed without moving the tip part 13. By the way, a plurality of NMR metering circuits may be provided in conformity with the number of the above mentioned antennae 82 and 83 or the antenna connected to one circuit may be switched.

By the way, in the first embodiment, the hood provided with an NMR metering antenna may be fixed to the tip part body 21 instead of being removably fitted or may be formed integrally with the tip part body.

The optical observing means may be provided with a television camera in the eyepiece part 4 of the endoscope 1.

Figure 11:
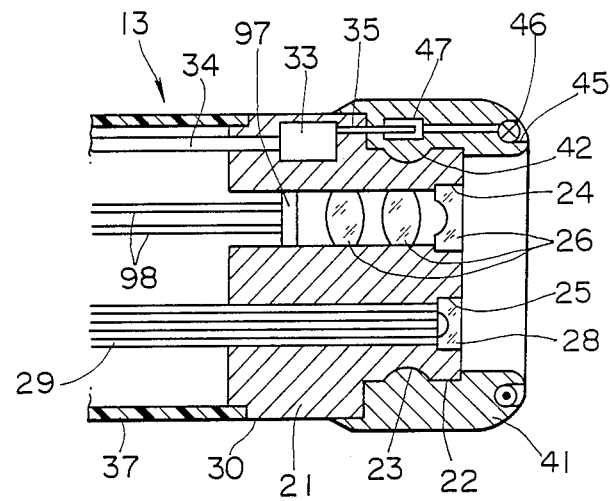
FIGS. 11 and 12 relate to the second embodiment of the present invention.
Figure 12:
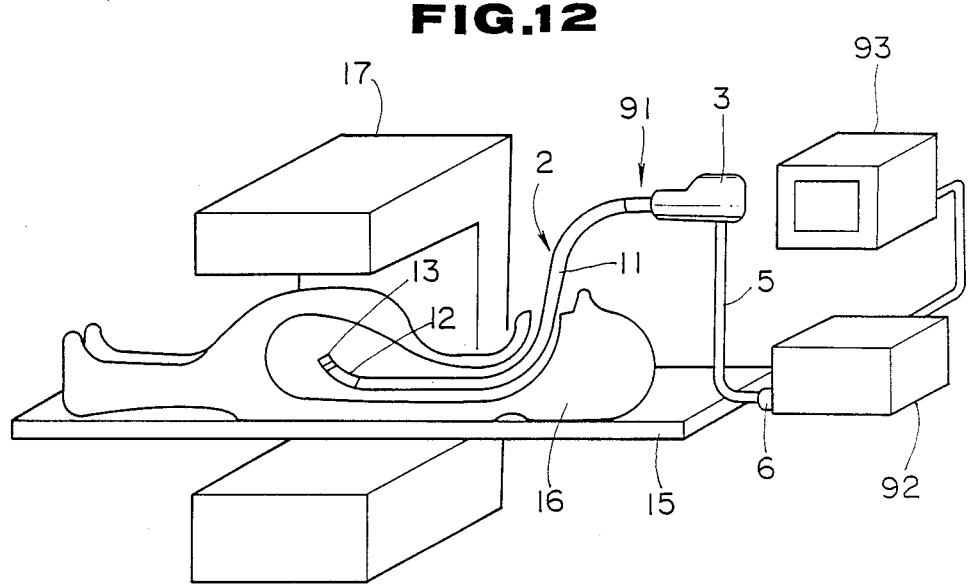

FIGS. 11 and 12 show the second embodiment of the present invention.

This embodiment is of an electronic endoscope.

As shown in FIG. 12, and NMR endoscope 91 is to be connected to a video processor 92 containing a light source apparatus and signal processing apparatus through a connector 6 provided at the tip of a universal cord 5. A monitor 93 is to be connected to the above mentioned video processor 92.

As shown in FIG. 11, in the above mentioned NMR endoscope 91, instead of the image guide 27, such solid state imaging device 97 as a CCD (charge coupled device) is arranged in the image forming position of the objective lens system 26. Signal lines 98 are connected to this solid state imaging device 97, are inserted through the insertable part 2, operating part 3 and universal cord 5 and are connected to the above mentioned connector 6. The above mentioned solid state imaging device 97 is to be connected to a signal processing circuit within the video processor 92 through the above mentioned connector. The above mentioned solid state imaging device 97 will be driven by the above mentioned signal processing circuit, the signal read out will be processed to be a video signal by the above mentioned signal processing circuit, the video signal output from this signal processing circuit will be input into the above mentioned monitor 93 and the object image will be displayed in this monitor 93.

A hood 41 provided with an antenna is to be fitted to the tip part 13 of the insertable part 2 in the same manner as in the first embodiment. By the way, in this embodiment, too, instead of the above mentioned hood 41, such various hoods as are shown in FIGS. 6 to 10 can be fitted.

By the way, the above mentioned NMR endoscope 91 is provided with no eyepiece part.

The other formations, operations and effects are the same as in the first embodiment.

As explained above, according to the first and second embodiments, as the NMR metering antenna is provided in the hood part of the tip part of the insertable part, there is an effect that the NMR metering antenna can be provided in the tip part without making the tip part large.

FIGS. 13 to 18 show the third embodiment of the present invention.

Figure 13:
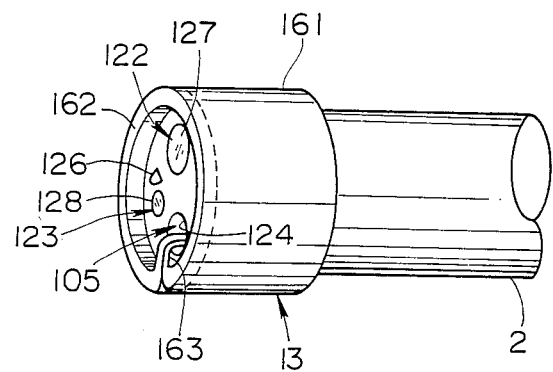
FIGS. 13 to 18 relate to the third embodiment of the present invention.

In this embodiment, as shown in FIG. 13, a hood 161 is to be removably externally fitted to the tip part 13 of the insertable part 2 of the endoscope 101.

Figure 14:
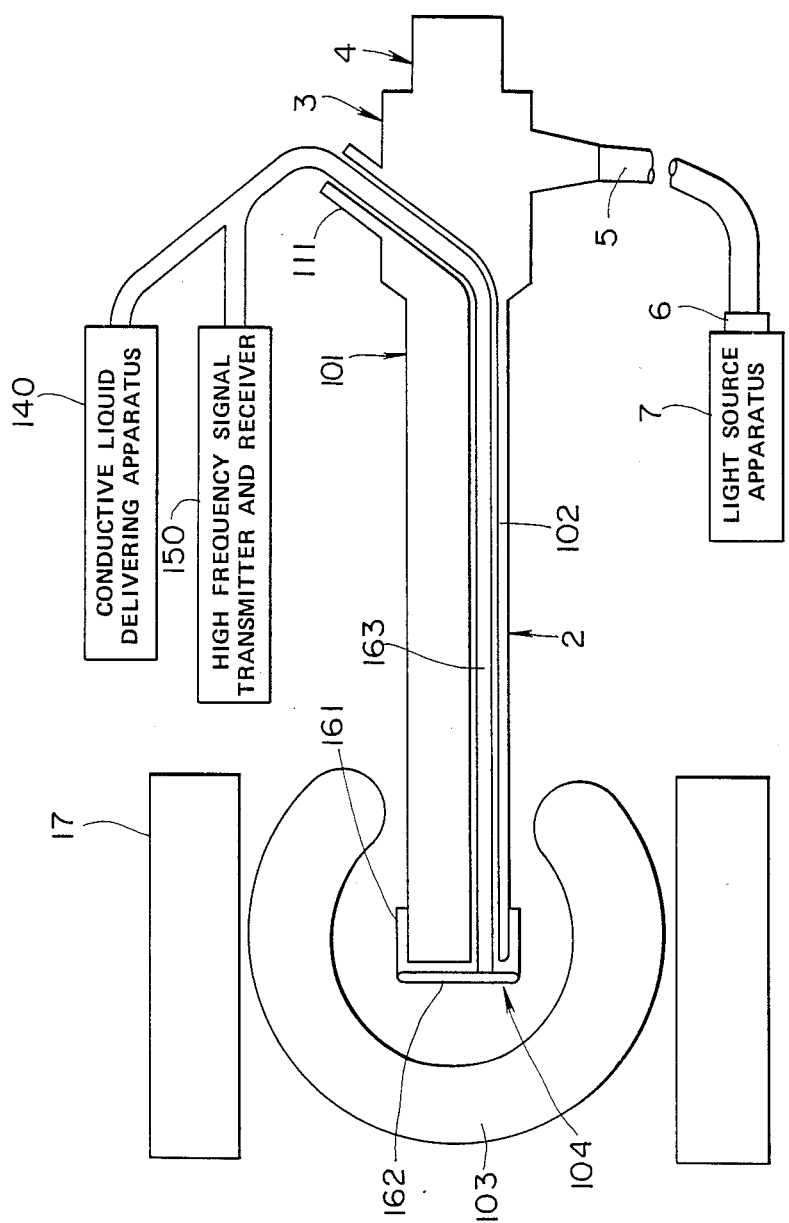

The above mentioned endoscope 101 of substantially the same formation as of the endoscope 1 of the first embodiment but, as shown in FIG. 14, a treating tool channel 102 is formed within the insertable part 2 and a leading inlet 111 communicating with the above mentioned treating tool channel 102 is provided in the operating part 3.

As shown in FIG. 13, an observing window 122, for example, a channel through hole 124, an air feeding nozzle not illustrated and water feeding nozzle 126 both opening toward the above mentioned observing window 122 are provided on the tip surfaces of the tip part 13. The above mentioned observing window 122 is fitted with an objective lens system 127 as an observing optical system. The tip surface of an image guide not illustrated inserted through the above mentioned insertable part 5 is arranged in the image forming position of this objective lens system 127. By the way, the optical axis of the above mentioned objective lens system 127 is substantially parallel with the axial direction of the insertable part 2 and is of a straight viewing type.

The above mentioned illuminating window 123 is fitted with a light distributing lens 128. A light guide not illustrated is arranged on the rear and side of this light distributing lens 128. A channel tube not illustrated forming the treating tool channel 102 is connected to the rear end side of the above mentioned channel through hole 124, is inserted through the above mentioned insertable part 2 and is connected to the above mentioned leading inlet 111. An air feeding channel tube and water feeding channel tube not illustrated are connected respectively to the above mentioned air feeding nozzle and water feeding nozzle 26, are inserted through the above mentioned insertable part 2 and universal cord 5 and are connected to the above mentioned connector 6.

By the way, in this embodiment, the insertable part 2 of the endoscope 1 is formed of such non-metal as plastics so that, even with the insertable part 2 left inserted within a body cavity 10, no influence may be given to the NMR apparatus observing from outside the body.

The other formations of the endoscope 101 are the same as of the first embodiment.

On the other hand, the hood 161 for protecting the above mentioned objective lens 127 and light distributing lens 128 is formed of such non-metal as plastics and has a loop like antenna part 162 made of an electrically insulative tube embedded on the tip side. For example, an antenna tube 163 inserted through the treating tool channel 102 is connected to this antenna part 162 and forms a circulating pipe line projecting out of the tip part 13 through the leading inlet 111 and treating tool channel 102 of the endoscope 101 from a conductive liquid delivering apparatus 140 provided outside the endoscope 101 and returning to the above mentioned conductive liquid delivering apparatus 140 through the above mentioned antenna part 162 and again through the treating tool channel 102 and leading inlet 111.

Figure 15:
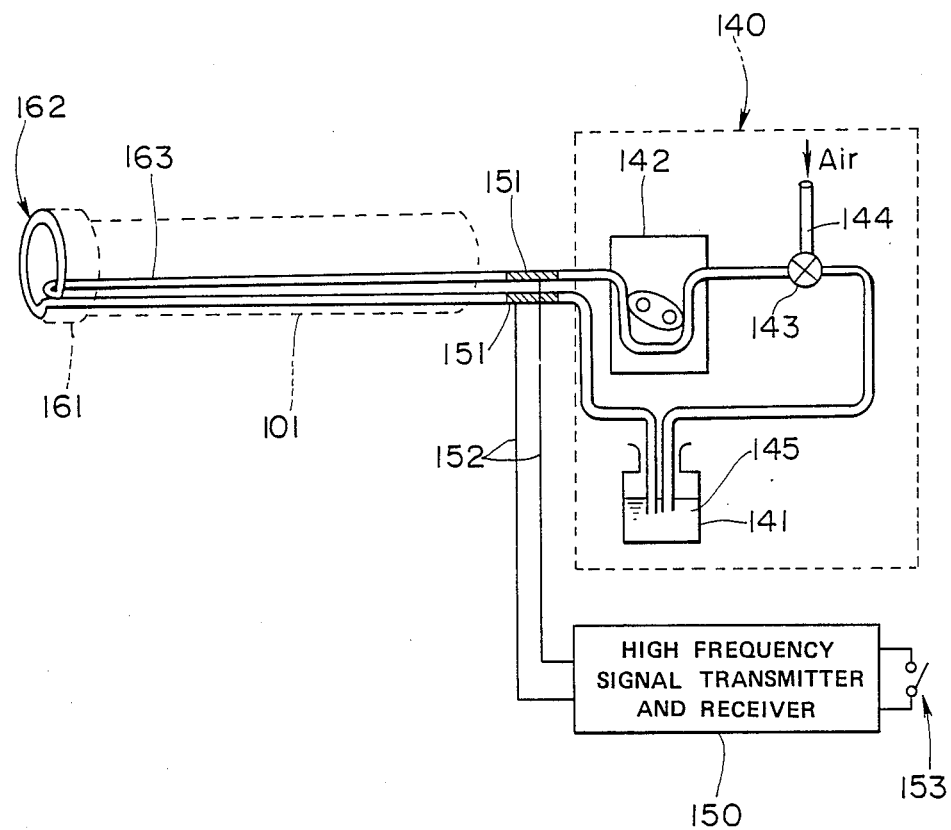

As shown in FIG. 15, the above mentioned conductive liquid delivering apparatus 140 is provided with a conductive liquid tank 141 interposed in the pipe line of the above mentioned antenna tube 163 and storing a conductive liquid 145 and a pump, for example, a rotary pump 142 for delivering a conductive liquid or air into the above mentioned antenna tube 163. The above mentioned conductive liquid tank 141 is provided on the inflow side of the above mentioned rotary pump 142 and a switching cock 143 is interposed in the antenna tube 163 between the conductive liquid tank 141 and rotary pump 142. An air inflow tube 144 is connected to the other inflow part of this switching cock 143. By switching the above mentioned switching cock 143, the conductive liquid 145 stored in the above mentioned conductive liquid tank 141 or air can be switched to flow into the above mentioned rotary pump 142. By the way, the above mentioned conductive liquid 145 as a fluid having a conductivity is such liquid having a conductivity as a solution of an electrolyte, for example, a saline solution.

As shown in FIG. 15, metallic tubes 151 are interposed in the parts led out of the leading inlet 111 of the above mentioned antenna tube 163 between the endoscope 101 and the above mentioned conductive liquid delivering apparatus 140 and are connected respectively with signal line 152 connected to a high frequency transmitter and receiver 150 which transmits high frequencies (currents) for metering NMR to the above mentioned signal lines 152 and receives NMR signals from the above mentioned signal lies 152. The above mentioned high frequency transmitter and receiver 150 is provided with a switch 153 switching on and off transmitted and received signals.

Figure 17:
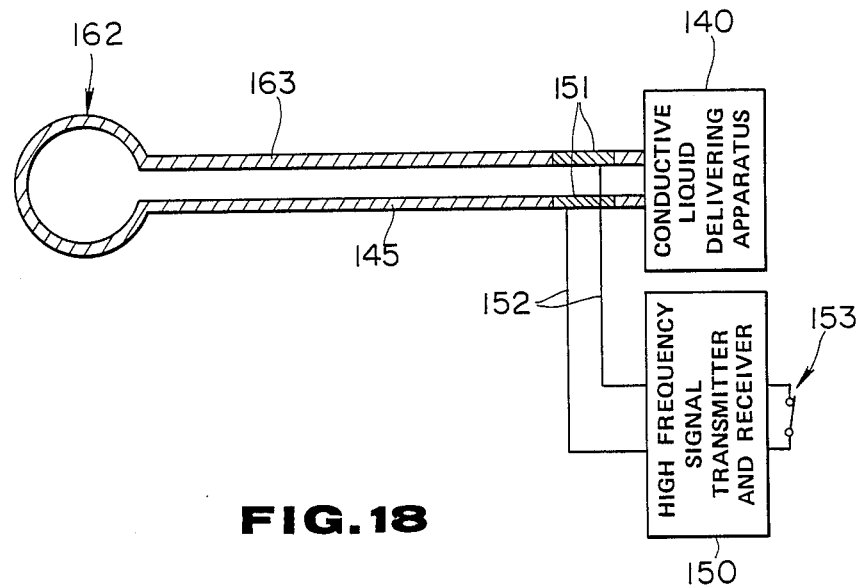

As shown in FIG. 17, in case the above mentioned antenna tube 163 is filled with the conductive liquid 145 by the above mentioned conductive liquid delivering apparatus 140, an NMR metering antenna will be formed of the conductive liquid 145. That is to say, the antenna tube 163 will have a conductivity and the antenna part 162 will function as an NMR metering antenna. This antenna part 162 is electrically connected to the high frequent transmitter and receiver 150 by the conductive liquid 145 within the antenna tube 163 and the signal lines 152.

Figure 18:
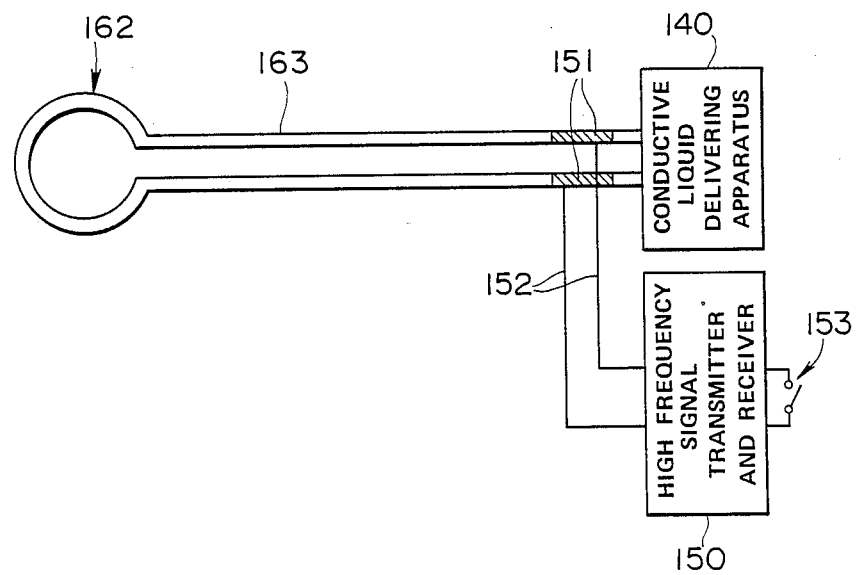

On the other hand, as shown in FIG. 18, when the switching cock 143 of the above mentioned conductive liquid delivering apparatus is switched to the air side, the above mentioned antenna tube 163 is filled with air and the above mentioned conductive liquid 145 is drained, the conductivity of the antenna tube 163 will be lost and the antenna part will no longer function as an NMR metering antenna.

Now, in the case of measuring NMR, as shown in FIG. 14, the endoscope 101 fitted with the above mentioned hood 161 is used as combined with the NMR apparatus 17 arranged to enclose the examinee 16. This NMR apparatus 17 is provided with such means generating a static magnetic field as a permanent magnet, paraconductive magnet or superconductive magnet. By the way, the above mentioned NMR apparatus 17 may be also an NMR imaging apparatus obtaining an NMR image from outside.

Figure 16:
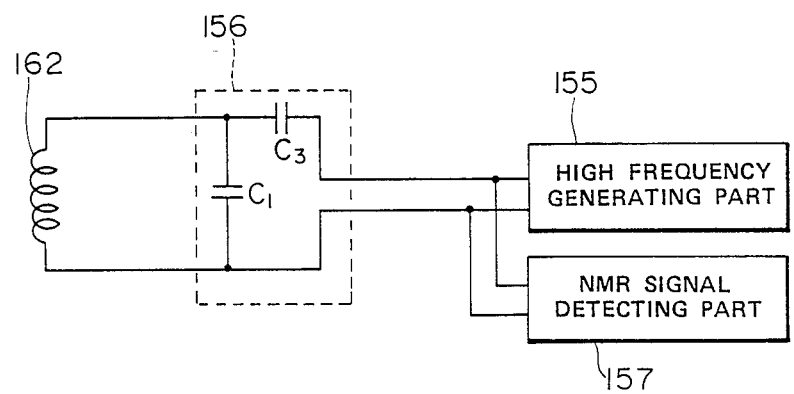

Now, the NMR metering means in this embodiment is formed as shown, for example, in FIG. 16.

That is to say, a high frequency corresponding to a metering object nucleus kind will be output from a high frequency generating part 155 within the above mentioned high frequency transmitter and receiver 150 and will be delivered to the antenna part 162 as filled with the conductive liquid 145 through the condenser part 156 and a high frequency magnetic field will be delivered to a living body from this antenna part 162. The above mentioned condenser part 156 is provided with a condenser $C_1$ in parallel with the above mentioned antenna part 162 and a condenser $C_3$ in series with the above mentioned antenna part 162 of which is formed matching circuit for matching the impedances on the above mentioned antenna part 162 side and high frequency transmitter and receiver 150 side.

In this embodiment, the above mentioned antenna part 162 transmits and receives signals, the NMR signal from the living body will be received by the above mentioned antenna part 162 and will be input into the NMR signal detecting part 157 within the above mentioned high frequency transmitter and receiver 150 through the above mentioned condenser part 156 and such information(NMR parameter) as the relieving time ($T_1$, $T_2$) will be obtained by this NMR signal detecting part 157.

The operation of this embodiment formed as in the above shall be explained in the following.

First of all, in case NMR is metered from within the body by using the endoscope 101 of this embodiment, as shown in FIG. 14, a static magnetic field is given to the examinee by the NMR apparatus 17. The hood 161 is fitted to the tip part 13 of the endoscope 101 and the antenna tube 163 is inserted through the treating tool channel 102 and is connected to the conductive liquid delivering apparatus 140 and high frequency transmitter and receiver 150. The insertable part 2 of the endoscope 101 is inserted into the body cavity 104 through the mouth cavity or the like of the examinee 103, an illuminating light is fed from the light source apparatus 7 to the light guide of the endoscope 101 and the object image by this illuminating light is observed from the eyepiece part 4. As shown in FIG. 17, the antenna tube 163 is filled with the conductive liquid 145 delivered by the conductive liquid delivering apparatus 140 and the antenna part 162 is contacted with the metering object position. The switch 13 of the high frequency transmitter and receiver 150 is switched on to deliver a high frequency to the antenna part 162 made to function as an NMR metering antenna having a conductivity by the above mentioned conductive liquid 145 and a high frequency magnetic field is delivered to the metering object position from this antenna part 162. When the NMR signal from the metering object position is received by the above mentioned antenna part and is metered by the NMR signal detecting part 157, the physiological variation of the metering object position, for example, whether it is a cancer or not will be able to be detected.

On the other hand, in the case of observing an NMR image from outside the body by using such NMR apparatus for obtaining an NMR image from outside the body as, for example, an NMR imaging apparatus, first of all, as shown in FIG. 18, the switch 153 of the above mentioned high frequency signal transmitter and receiver 150 is switched off to stop metering NMR from within the body. With the endoscope 101 left inserted within the body cavity 104, the switching cock 143 of the above mentioned conductive liquid delivering apparatus 140 is switched to the air side, as shown in FIG. 18, to fill the above mentioned antenna tube 163 with air and drain the above mentioned conductive liquid 145. Then, the conductivity of the antenna part 162 and antenna tube 163 will be lost. Therefore, the magnetic field of the NMR apparatus for observation from outside the body will not be disturbed by the above mentioned antenna part 162 and antenna tube 163 and a favorable NMR image from outside the body will be obtained.

Thus, in this embodiment, when antenna part 162 and antenna tube 163 are filled with the conductive liquid 145, an NMR metering antenna will be formed and, when the conductive liquid 145 is drained out of the above mentioned antenna part 162 and antenna tube 163, the NMR apparatus for observation from outside the body will not be influenced.

Therefore, when the endoscope apparatus of this embodiment is used, in case the NMR apparatus for observing from outside the body is also used, even if the endoscope 101 is not pulled out of the body cavity 104, a favorable NMR image from outside the body will be able to be obtained.

Also, according to this embodiment, the antenna part 162 can be provided in the tip part 13 at a high space efficiency.

By the way, in this embodiment, the conductive fluid is not limited to be such liquid as a saline solution but may be a conductive gel, an ionized gas, such conductive powder as a metal powder or a mixture of these.

The shape of the antenna part is not limited to be like a single winding loop but may be any of such various shapes as a saddle shape as shown in the first embodiment and its modifications.

By the way, the endoscope is not limited to be a fiber scope but may be an electronic scope provided with a solid state imaging device as an imaging means as in the second embodiment and is not limited to be a flexible endoscope but may be a rigid endoscope.

Figure 19:
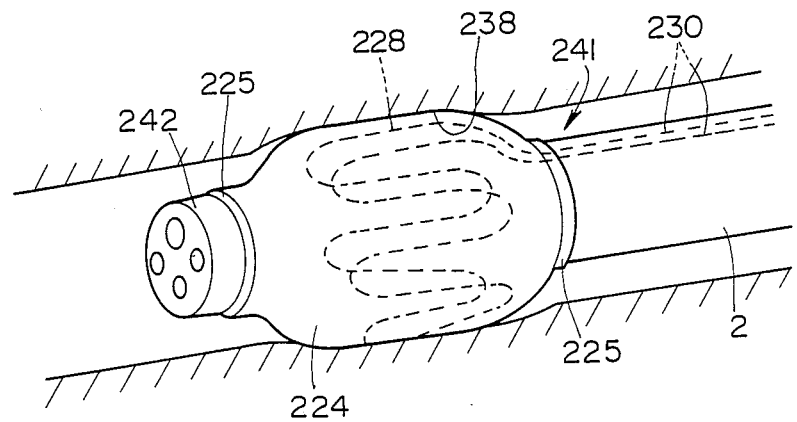
FIGS. 19 to 21 relate to the fourth embodiment of the present invention.
Figure 20:
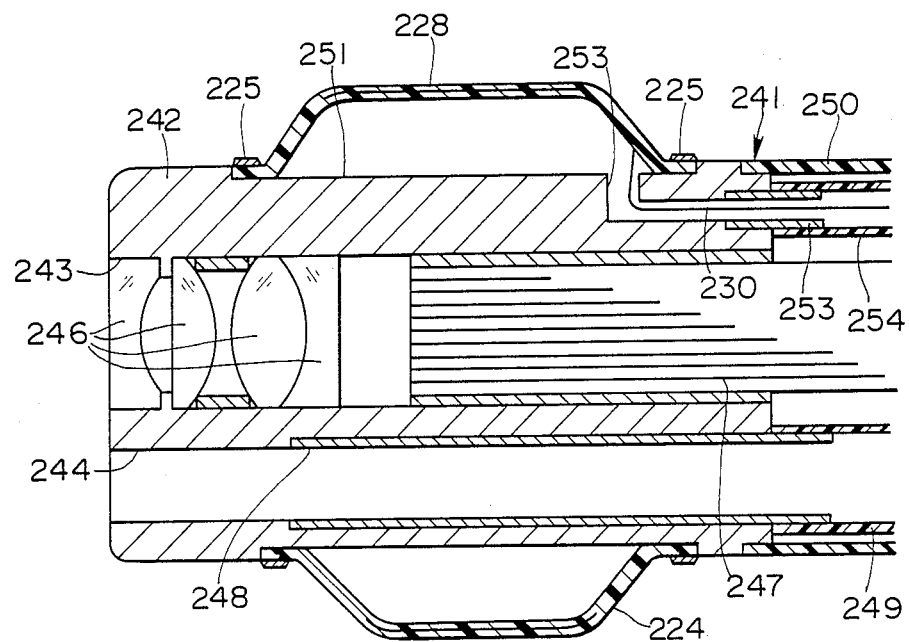
Figure 21:
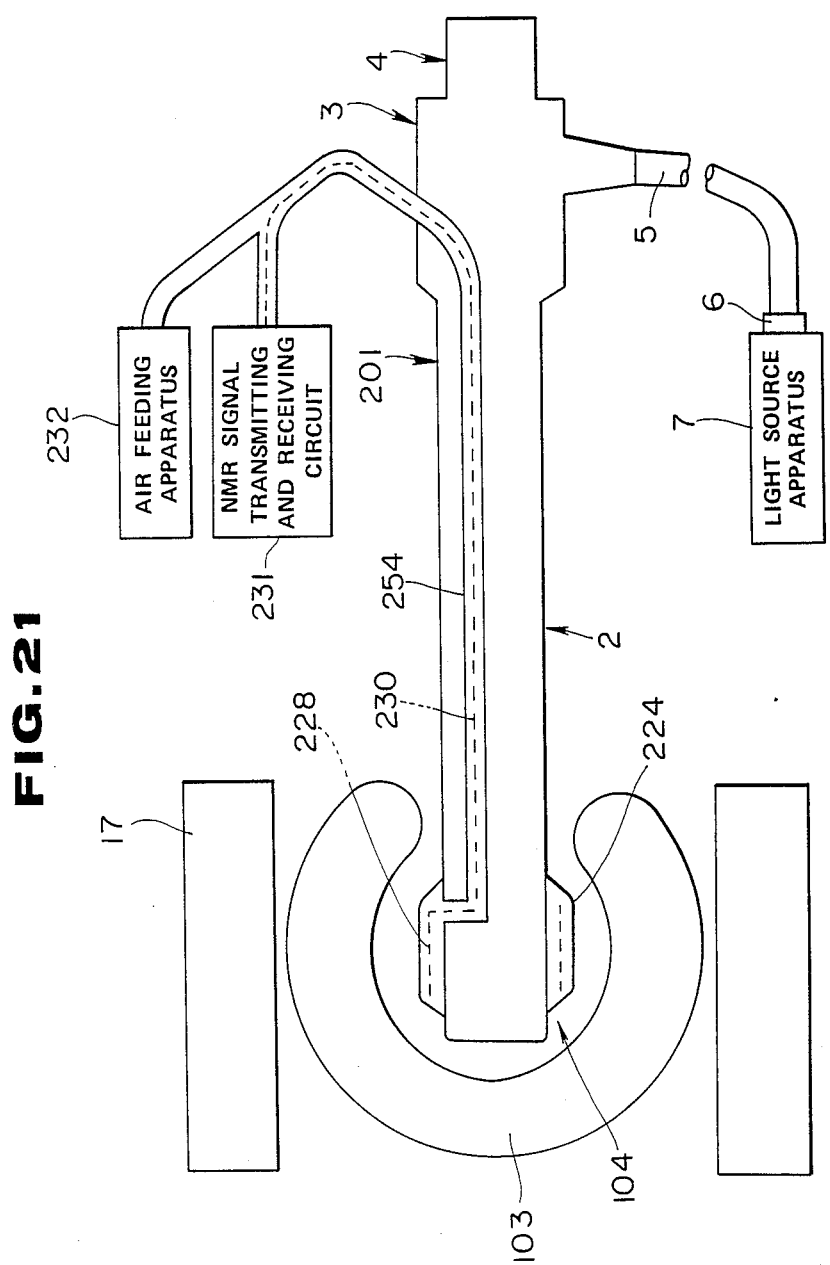

FIGS. 19 to 21 show the fourth embodiment of the present invention.

In this embodiment, a balloon 224 in which an NMR metering antenna 228 is embedded is provided on the outer periphery of the tip part 241 of the insertable part 2 of an endoscope 201. As shown in FIG. 20, the above mentioned tip part 241 is provided, for example, with a rigid substantially columnar tip part body 242 in which are formed an observing through hole 243, treating tool channel though hole 244 and illuminating through hole not illustrated passing parallelly in the axial direction of the insertable part 2. The above mentioned observing through hole 243 is fitted with an objective lens system 246 on the tip side. The tip surface of an image guide 247 inserted through the above mentioned insertable part 2 and fitted at the tip into the above mentioned observing through hole 243 is arranged in the image forming position of this objective lens system 246. The above mentioned illuminating through hole is fitted with a light distributing lens not illustrated. A light guide not illustrated is arranged on the rear end side of this light distributing lens. A channel pipe 248 is fitted on the rear end side of the above mentioned treating tool channel through hole 244. A channel tube 249 forming the treating tool channel is connected to the rear end part of this channel pipe 248. A flexible tube 250 forming the outer cover of the insertable part 2 is connected to the rear end of the above mentioned tip part body 242.

A wide groove 251 is peripherally formed on the outer periphery of the above mentioned tip part body 242. An extensible balloon 224 is fitted to this groove 251 by fixing members 225. An air passing hole 253 communicating with the interior of the above mentioned balloon 224 is provided inside the above mentioned tip part 242. This air passing hole 253 is bent to the rear end side of the tip part body 242. An air feeding tube 254 is connected to the rear end of this air passing hole 253. As shown in FIG. 21, this air feeding tube 254 is inserted through the above mentioned insertable part 2, is led, for example, out of the operating part 3 and is connected to an air feeding apparatus 232. An NMR metering high frequency antenna 228 is embedded within the film forming the above mentioned balloon 224. For example, as shown in FIG. 19, this antenna 228 is arranged over the entire periphery of the above mentioned balloon 224 while bending alternately in the reverse directions of the axial direction. The above mentioned antenna 228 is connected at both ends to cables 230 inserted, for example, through the above mentioned air feeding tube 254 and connected to an NMR signal transmitting and receiving circuit 231.

By the way, a high frequency generating part 155 and NMR signal detecting part 157 are provided within the above mentioned NMR signal transmitting and receiving circuit 231. The formation of the NMR metering means is the same as is shown in FIG. 16.

The operation of this embodiment shall be explained in the following.

As shown in FIG. 21, a static magnetic field is given to the examinee 103. The insertable part 2 of the endoscope 201 with the balloon 224 contracted is inserted into the body cavity 104 through the mouth cavity or the like of the examinee 103, an illuminating light is fed to the light guide of the endoscope 201 from the light source and the object image by this illuminating light is observed from the eyepiece part 4. In the case of metering NMR within a pipe cavity or the like, as shown in FIG. 19, air is fed to the air feeding tube 254 from the air feeding apparatus 232 to inflate the balloon 224 and this balloon is fixed to the metering object position 238. The antenna 228 embedded in this balloon 224 will be also fixed to the metering object position 238. In this state, a high frequency will be delivered to the above mentioned antenna 228 from the high frequency generating part 155 and a high frequency signal will be delivered to the metering object position 238 from this antenna 228. When the NMR signal from the metering object position 238 is received by the above mentioned antenna 228 and is metered by the NMR signal detecting part 157, the physiological variation, for example, whether it is a cancer or not will be able to be detected.

In this embodiment, when the tip part 241 of the insertable part 2 is inserted into the metering object position and the above mentioned balloon 224 is inflated and is fixed to the object position within the body cavity, the antenna 228 provided in this balloon 224 will be able to be easily fixed to the object position within the body cavity.

Also, according to this embodiment, the antenna 228 can be provided on the outer periphery of the tip part 241 of the insertable part 2 at a high space efficiency and the insertable part 2 can be made small in the diameter.

Also, according to this embodiment, the entire periphery of the balloon 224 as fixed can be metered by once.

Figure 22:
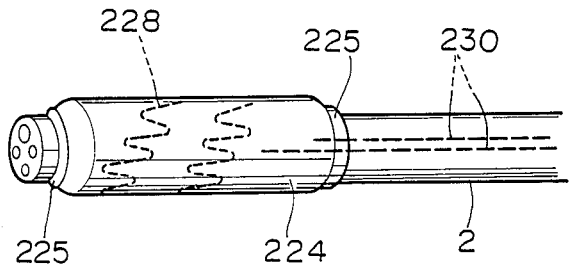
FIGS. 22 and 23 relate to the first modification of the fourth embodiment.
Figure 23:
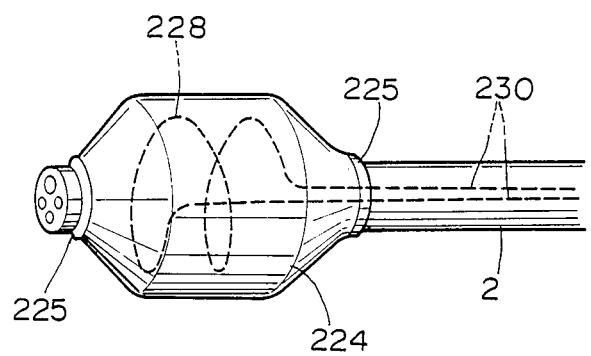

FIGS. 22 and 23 show the first modification of the fourth embodiment.

In this modification, as shown in FIG. 23, the antenna 228 is provided so as to be spiral, for example, of two turns when the balloon 224 is inflated. As shown in FIG. 22, the above mentioned antenna 228 is flexible enough to be able to contract the balloon 224 so that the antenna 228 will bend, for example, finely alternately when the balloon 224 is contracted.

By the way, only the front side part of the antenna 228 is shown in FIG. 22.

The other formations, operations and effects are the same as in the fourth embodiment.

Figure 24:
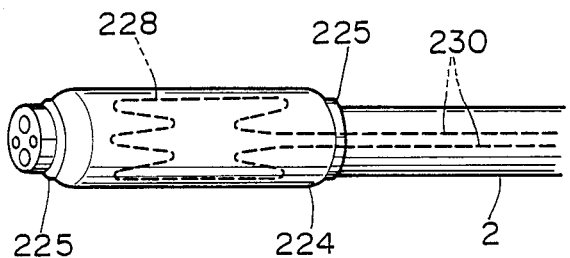
FIGS. 24 and 25 relate to the second modification of the fourth embodiment.
Figure 25:
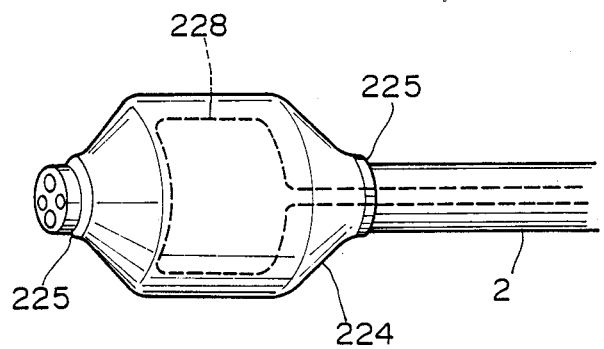

FIGS. 24 and 25 show the second modification of the fourth embodiment.

In this modification, as shown in FIG. 25, an antenna 228 is provided so as to be arranged like a saddle on one side of the diametral direction when the balloon 224 is inflated. The same as in the first modification, as shown in FIG. 24, the above mentioned antenna 229 is flexible enough to be able to contract the balloon 224 so that the antenna 228 will bend, for example, finely alternately when the balloon 224 is contracted.

The other formations, operations and effects are the same as in the fourth embodiment.

By the way, in the fourth embodiment, the balloon 224 in which the antenna 228 is embedded may be removably fitted to the endoscope.

The antenna 228 may be fitted to the outer periphery or inner periphery of the balloon 224.

The shape of the antenna 228 is not limited to be as shown in the above mentioned embodiment and respective modifications but may be like saddles wound on both sides of the diametral direction or a one-wind loop.

By the way, the endoscope is not limited to be a fiber scope but may be an electronic scope provided with a solid state imaging device as an imaging means as in the second embodiment and is not limited to be a flexible endoscope but may be a rigid endoscope.

Figure 26:
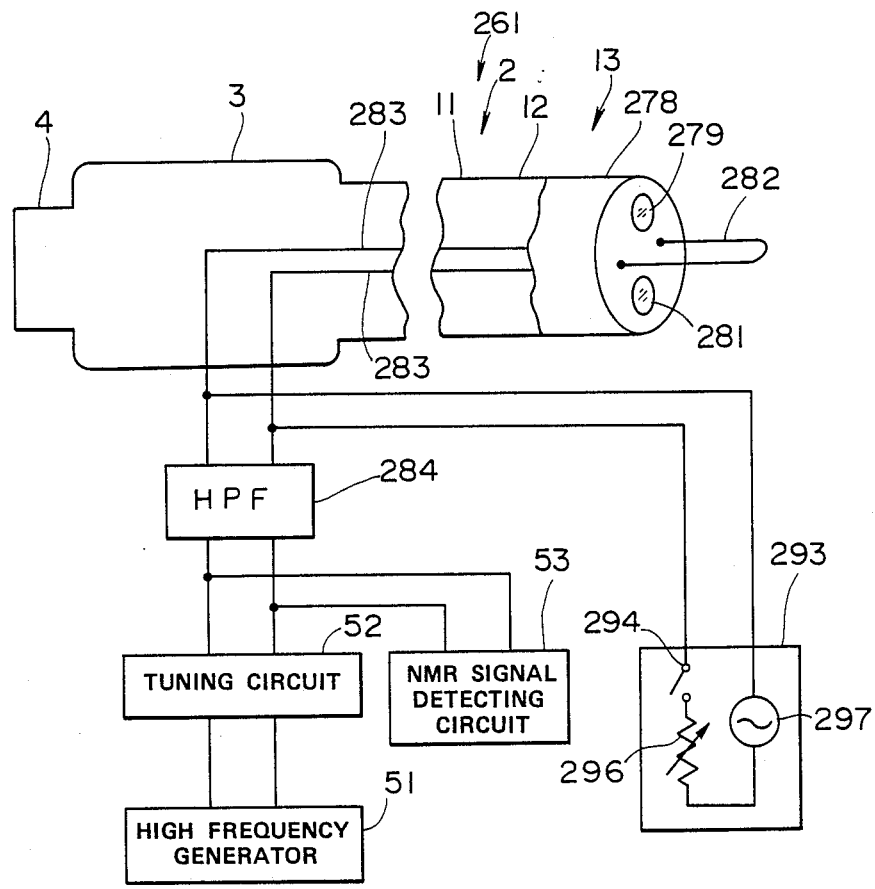

FIGS. 26 and 27 show the fifth embodiment of the present invention.

As shown in FIG. 26, the tip part 13 of the endoscope 261 of this embodiment is provided with a substantially columnar tip part body 278 made of such rigid material as a metal.

An objective lens system 279 which can form an observed image on the entrance end surface of an image guide not illustrated transmitting the observed image to the eyepiece part 4 and a light distributing lens system 281 which can feed the illuminating light from the above mentioned light source apparatus 7 to an observed position through a light guide not illustrated are provided on the front end surface of the above mentioned tip part body 278.

Further, an NMR metering antenna 282 formed to be like a letter U of such form memorizing alloy as a Ti—Ni type or Cu—Zn—Al type alloy which is a thermotransformable member is provided on the tip surface of the tip part body 278. Signal lines 283 connected to both ends of this antenna 282 are inserted through the insertable part 2 and are led to the operating part 3. By the way, the antenna 282 is coated with an adiabatic member.

The above mentioned form memorizing alloy transformed in the martensite phase will return to be of the original form memorized in the austenite phase in case the martensite phase (low temperature side) is reversely converted to the austenite phase (high temperature side). The form memorizing alloy to be used in this embodiment is of two directions memorizing not only the form in the austenite phase but also another form in the martensite phase and reversibly varies in the form in response to the temperature fluctuation.

In the case of this embodiment, the NMR metering antenna 282 memorizes such U form formed in the lengthwise direction of the insertable part 2 as is represented by the one-point chain line in FIG. 27(A) in the martensite phase (low temperature side) and memorizes such form at right angles with the lengthwise direction of the insertable part 2 as is represented by the solid line in FIG. 27(B) in the austenite phase (high temperature side).

The above mentioned signal lines 283 led to the operating part 3 are extended out of the operating part 3, are inserted through the above mentioned universal cord 5 and are connected to a high-pass filter 284 and a heating circuit 293 as a form converting means provided within the light source apparatus 7. The high-pass filter 284 is connected to a tuning circuit 52 and NMR signal detecting circuit 53. Further, the tuning circuit 52 is connected to the output end of a high frequency generator 51. The heating circuit 293 is connected with a switch 294, variable resistor 296 and current source 297 so as to be able to heat the NMR metering antenna 282.

The NMR metering means including the above mentioned antenna 282 is the same as is shown in FIG. 5.

The other formations are substantially the same as in the first embodiment.

The operation of this embodiment formed as in the above shall be explained in the following.

As in FIG. 2, the examinee 16 is mounted on the bed 15 and a static magnetic field is given to the examinee 16 by the NMR apparatus 17. In this state, the insertable part 2 of the endoscope 261 provided with the NMR metering antenna 282 is inserted through the mouth cavity or the like of the examinee 16, an illuminating lights is fed to a light guide not illustrated of the endoscope 261 and the upper layer part or the like of the stomach wall is observed with the observing optical system consisting of the objective lens system 279, image guide not illustrated and eyepiece part 4. In case an abnormal position 299 is discovered, for example, in the front surface in the inserting direction, the switch 294 of the heating circuit 293 provided in the light source apparatus 7 is closed to pass electricity to the NMR metering antenna 282. In this case, the temperature rise of the antenna 282 can be made slow by controlling the variable resistor 296.

In FIG. 27(A), the antenna 282 represented by the one-point chain line shows the state before heating. When the temperature of the antenna 282 rises due to the passing of electricity and becomes the temperature (called an As point) at which a reverse transformation to the austenite phase starts, the form will begin to be transformed. When the temperature (called an Af point) at which the reverse transformation finishes is reached, a form bending at right angles with the lengthwise direction of the insertable part 2 will be made. Thus, the direction of the high frequency magnetic field generated by the antenna 282 and the detecting direction can be made to coincide with each other. In this state, a high frequency is delivered to the above mentioned antenna 282 through the high frequency generator 51, tuning circuit 52 and condenser box 33 and a high frequency magnetic field is output to the abnormal position 299 from this antenna 282. By the way, it is desirable that the direction of this high frequency magnetic field intersects at right angles with the direction of the static magnetic field. When the NMR signal from the abnormal position 299 is received by the above mentioned antenna 282 and is metered by the NMR signal detecting circuit 53, the physiological variation of the abnormal position 299, for example, whether it is a cancer or not will be able to be detected.

In case the abnormal position 299 has an inclination to the inserting direction as in FIG. 27(B), the bending angle can be controlled by controlling the heating amount with the variable resistor 296 so as to keep the temperature of the antenna 282 below the Af point.

After the end of the detection, the switch 294 is opened to stop passing electricity. The antenna 282 will be naturally cooled, will be reduced in the temperature, will be transformed to be in the martensite phase and will return to be in the U-like form formed in the lengthwise direction of the insertable part 2 and memorized in the martensite phase shown by the one-point chain line in FIG. 27(A).

By the way, in this embodiment, electricity is passed directly to the antenna 282 but the temperature of the antenna 282 may be controlled by using such heating device as a Zener diode near the antenna 282.

Also, the antenna 282 may be bent by Joule heat produced by the high frequency without providing the heating circuit 293.

Further, in this embodiment, the antenna 282 is formed of a form memorizing alloy but may be formed of a bimetal or the like made by pasting together two kinds of metals different in the coefficient of expansion.

In this embodiment, the NMR metering antenna 282 and signal lines 283 are fixed within the insertable part 2 but may be inserted through the treating tool channel or the like and may be made removable.

FIG. 28 shows a modification of the fifth embodiment.

The tip part body 278 provided in the tip part 13 of the insertable part 2 is provided with an objective lens system 279 as an observing optical system and a light distributing lens system 281 as an illuminating optical system. An NMR metering antenna 300 formed to be like a plurality of wound loops of a form memorizing alloy as in FIG. 28(A) is provided forward of the tip part body 279 and is to be heated by a heating circuit not illustrated. When the antenna 300 is heated and the heating temperature passes through the As point and then through the Af point, the reverse transformation will finish and the antenna 300 will bend to be in the form memorized in the austenite phase as in FIG. 28(B). Thus, the direction of the high frequency magnetic field can be changed to coincide with the detecting direction.

As explained above, according to this embodiment, by bending the NMR metering antenna, the direction of the high frequency magnetic field generated by the antenna and the detecting direction can be easily made to coincide with each other and a quick diagnosis can be made.

By the way, the shape of the antenna is not limited to be as shown in the above mentioned embodiment and modification but may be like saddles wound on both sides of the diametral direction or like a single winding loop.

By the way, the endoscope is not limited to be a fiber scope but may be an electronic scope or the like provided with a solid state imaging device as an imaging means as in the second embodiment and is not limited to be a flexible endoscope but may be a rigid endoscope.

Figure 29:
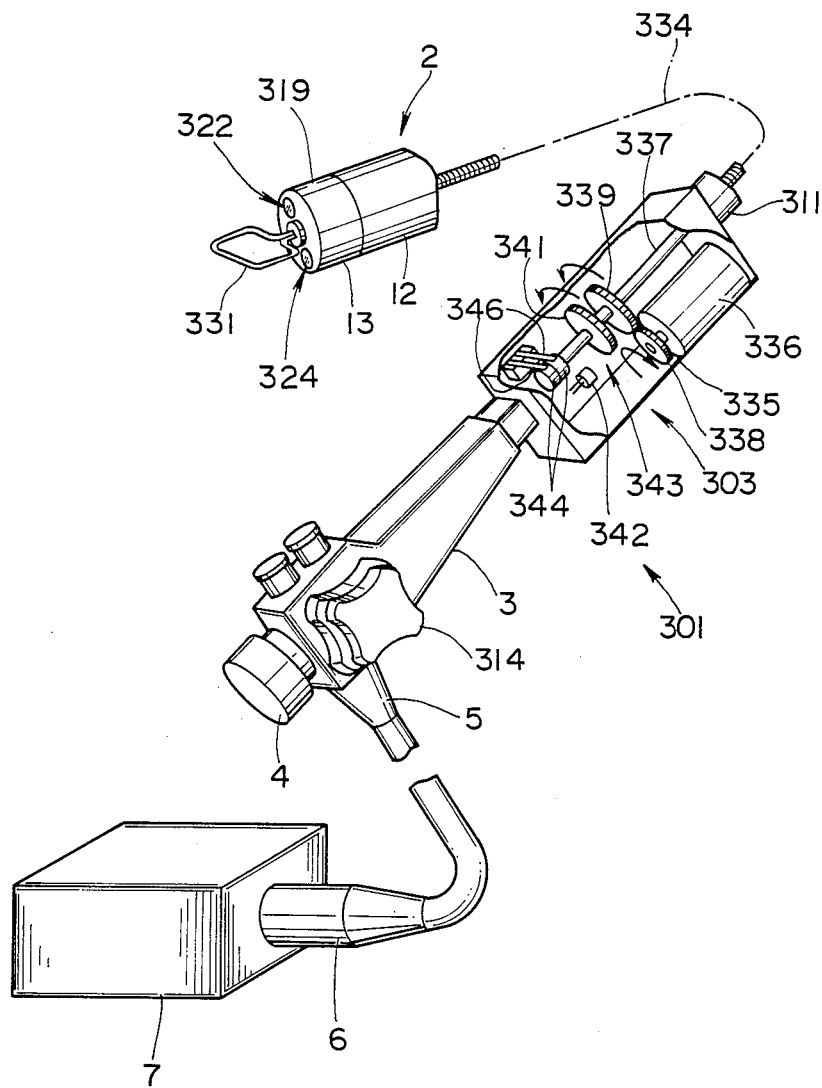
FIGS. 29 to 31 relate to the sixth embodiment of the preset invention.
Figure 30:
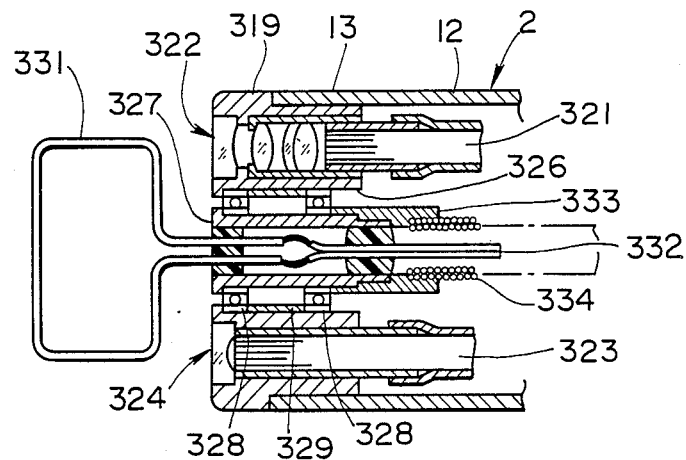
Figure 31:
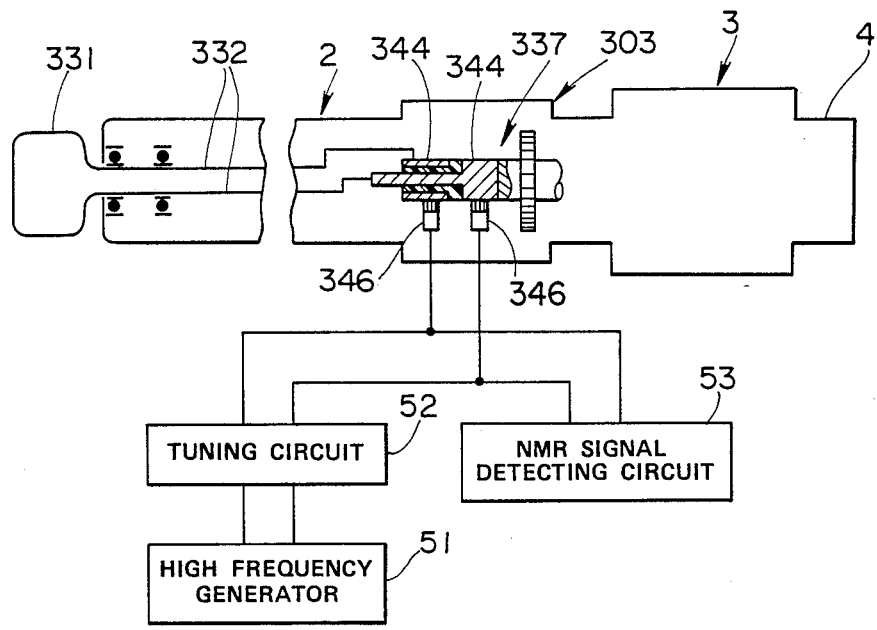

FIGS. 29 to 31 show the sixth embodiment of the present invention.

As shown in FIG. 29, an endoscope 301 of this embodiment is provided with an elongate, for example, flexible insertable part 2 and antenna driving part 303 internally fitted with a driving means and connected to the rear end of this insertable part 2, a thick operating part 3 connected to the rear end of the above mentioned antenna drivinq part 303, an eyepiece part 4 connected to the rear end of the above mentioned operating part 3 and a flexible universal cord extended from the side part of the operating part 3 and provided with a connector 6 at the tip so that the endoscope 301 may be connected through the above mentioned connector 26 to a light source apparatus 7 containing, for example, an NMR metering apparatus.

The same as in the first embodiment, the above mentioned insertable part 2 is formed of a curvable part 12 connected to the tip of a flexible part 11 provided on the operating part 3 side and a tip part 13 connected to the tip of this curvable part 12.

The above mentioned curvable part 12 can be curved vertically and horizontally by rotating a curving operation knob 314 provided on the above mentioned operating part 3.

In the case of metering NMR, the above mentioned endoscope 30 is used as combined with the NMR apparatus 17 arranged to enclose the examinee mounted on the bed 15 as shown in FIG. 2.

As shown in FIG. 30, the tip part 13 of the endoscope 301 is provided with a substantially columnar tip part body 319 made of such rigid material as a metal.

An objective lens system 322 as such observing optical system as can form an observed image on the entrance end surface of an image guide 321 transmitting the observed image to the eyepiece 4 and a light distributing lens system 324 as an illuminating optical system which can feed the illuminating light from the above mentioned light source apparatus 7 to the observed position through a light guide 323 are provided on the front end surface of the above mentioned tip part body 319.

Further, a driving shaft through hole 326 parallel with the lengthwise direction of the insertable part 2 is provided in the central part of the tip part body 319. A tubular rotary part 327 is borne by ball bearings 328 within this driving shaft through hole 326. By the way, a tubular spacer 329 is inserted between the ball bearings 328. An NMR metering antenna 331 having a contour equal to or somewhat smaller than the outside diameter of the tip part body 319 provided forward of the tip part 13 and formed to be substantially square is fixed at both ends by a resin or the like to the front part of the inner periphery of the above mentioned rotary member 327. Further, signal lines 332 inserted through the insertable part 2 and led to the antenna driving part 303 are fixed by a resin or the like to the rear part of the inner periphery of the rotary member 327 and are electrically connected to both ends of the above mentioned antenna 331.

A cylindrical connecting member 333 is externally fitted to the rear end of the above mentioned rotary member 327 so as to contact at the front end with the inner race of the above mentioned ball bearing 328. A driving shaft 334 inserting the above mentioned signal lines 332, inserted through the insertable part 2 and led to the antenna driving part 303 is connected to the rear end of the above mentioned rotary member 327. This driving shaft 334 is made, for example, by spirally closely winding a metallic wire and further spirally closely winding thereon a metallic wire in a different winding direction, is flexible and can transmit a torque.

A motor 336 as a driving means having a reduction gear is provided within a case 335 forming the above mentioned antenna driving part 303, is connected to the above mentioned driving shaft 334 through gears 338 and 339 and drives a connecting shaft 337 provided parallelly with the rotation center of the motor 336.

The connecting shaft 337 is provided with an encoder 343 formed of a rotary disc 341 and photosensor 342.

As shown in FIG. 31, the signal lines 332 extended out of the NMR metering antenna 331 are connected to electric contacts 344 provided in the rear end part of the connecting shaft 337. One of these electric contacts is a rod-like core member and the other is formed of a tubular member inserting this core member through an insulative member. Further, the electric contacts 344 electrically contact respective brushes 346 fixed to the case 335. These brushes 346 are connected to the tuning circuit 52 and NMR signal detecting circuit 53 provided within the light source apparatus 7 through the operating part 3 and universal cord 5. The above mentioned tuning circuit 52 is connected to the output end of the high frequency generator 51.

The NMR metering means including the above mentioned antenna 331 is the same as is shown in FIG. 5.

The operation of this embodiment formed as in the above shall be explained in the following.

As in FIG. 2, the examinee 16 is mounted on the bed 15 and a static magnetic field is given to the examinee by the NMR apparatus 17. In this state, the insertable part 2 of the endoscope 301 provided with the NMR metering antenna 331 is inserted through the mouth cavity or the like of the examinee 16, an illuminating light is fed to the light guide 323 of the endoscope 301 and the upper layer part or the like of the stomach wall is observed with the observing optical system consisting of the objective lens system 322, image guide 321 and eyepiece 4. In case an abnormal position is discovered, for example, in the upper layer part of the stomach wall, the motor 336 of the antenna driving part 303 is driven to make the direction of the high frequency magnetic field generated by the NMR metering antenna 331 directed toward the tip part 13 and the detecting direction coincide with each other. In this state, a high frequency is delivered to the above mentioned antenna 331 through the high frequency generator 51, tuning circuit 52 and condenser box 33 and a high frequency magnetic field is output to the abnormal position from this antenna 331. By the way, it is desirable that the direction of this high frequency magnetic field intersects at right angles with the static magnetic field. When the NMR signal from the abnormal position is received by the above mentioned antenna 331 and is metered by the NMR signal detecting circuit 53, the physiological variation, for example, whether it is a cancer or not will be able to be detected.

As explained above, according to this embodiment, there are effects that, by making the NMR metering antenna rotatable, the direction of the high frequency magnetic field generated by the antenna and the detecting direction can be easily made to coincide with each other and a quick diagnosis can be made.

By the way, in the above mentioned embodiment, a driving means is provided near the operating part but, for example, a motor or the like may be incorporated in the tip part of the endoscope to make the antenna rotatable.

By the way, the endoscope is not limited to be a fiber scope but may be an electronic scope or the like provided with a solid state imaging device as an imaging means as in the second embodiment and is not limited to be a flexible endoscope but may be a rigid endoscope.

Figure 32:
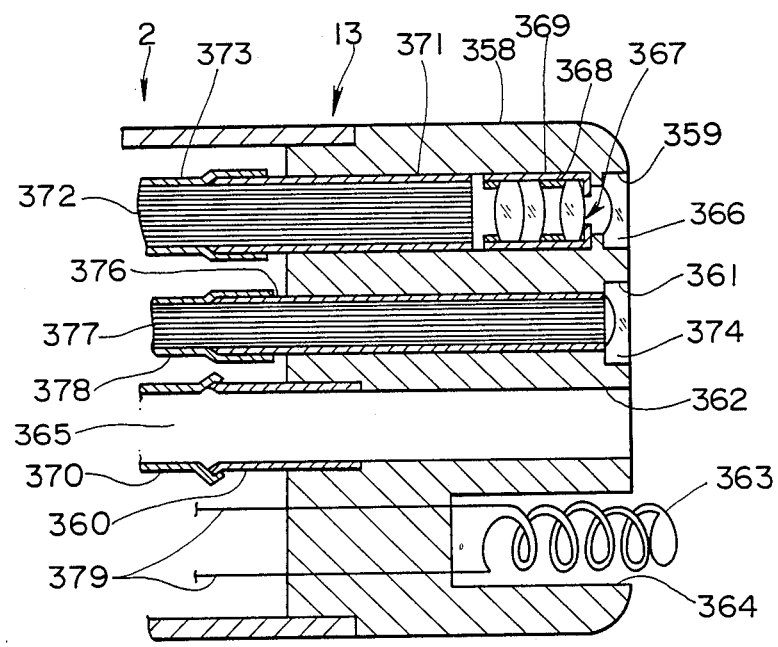
FIG. 32 is a sectioned view of the tip pat of the insertable part of an endoscope in the seventh embodiment of the present invention.

FIG. 32 shows the seventh embodiment of the present invention.

In the endoscope of this embodiment, an observing through hole 359, an illuminating through hole, a forceps channel through hole and an NMR metering antenna 363 containing den 364 are provided parallelly with the lengthwise direction of the insertable part 2 in a tip part body 358 provided in the tip part 13 of the insertable part 2.

An objective lens 366 is fitted in the tip part of the above mentioned observing through hole 359. A lens frame 369 fixing an image forming lens system 367 with a spacer 368 is fitted in the rear of this objective lens 366. The entrance end surface of an image guide 372 inserted in a connecting pipe 371 is provided in the image forming position of the image forming lens system 367. By the way, the image guide 372 is coated with a coating tube 373. The tip part of this coating tube 373 externally fits the outer periphery of the connecting pipe 371.

A light distributing lens 374 is fitted to the front part of the above mentioned illuminating through hole 361. A light guide 377 inserted through a connecting pipe 376 is provided in the rear of the light distributing lens 374. The rear end part of the connecting pipe 376 is externally fitted with the front end part of a coating tube 378 coating the light guide 377.

A forceps channel tube 370 forming a forceps channel 365 is connected with a connecting pipe 360 in the rear of the above mentioned forceps channel through hole 362. Further, an NMR metering antenna 363 projecting in the front part out of the front end surface of the tip part body 358 is provided within the above mentioned den 364. This antenna 363 is spirally formed of a plurality of windings of two conductors connected together at the front ends, inserted at the rear ends through the insertable part 2 and connected with signal lines 379 passed through the tip part body 358.

The other formations are the same as in the first embodiment.

In this embodiment, in the case of metering NMR, when the above mentioned antenna 363 is pushed against an object position, the antenna an object position, the antenna will maintain will be energized and will be supported and fixed in the object position by the energizing force produced then.

Thus, according to this embodiment, as the NMR metering antenna to be inserted into the body cavity through the endoscope is made resilient, there are effects that the antenna can be supported and fixed in the detected position within the body cavity and an accurate metering can be easily made.

Also, according to this embodiment, as the antenna 363 is provided in the tip part body 358 of the endoscope, by only operating the tip part body 358 of the endoscope with a curving operation knob not illustrated, the antenna 363 can be pushed against the detected position and the operatability improves.

Figure 33:
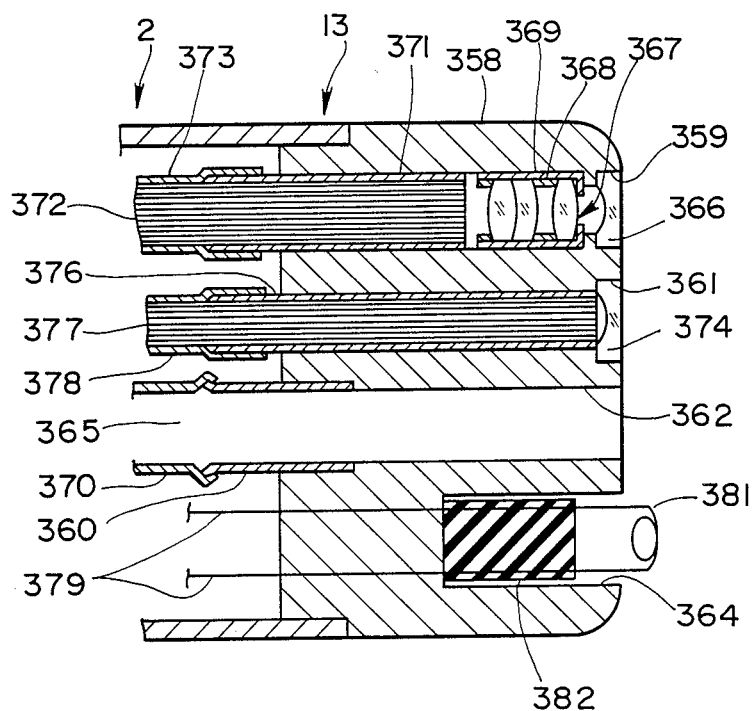
FIG. 33 is a sectioned view of the tip part of the insertable part of an endoscope in a modification of the seventh embodiment.

FIG. 33 shows a modification of the seventh embodiment.

In this embodiment, instead of the resilient antenna 363, an antenna 381 is fixed in a den 364 through a resilient supporting member 382.

The other formations, operations and effects are the same as in the seventh embodiment.

By the way, in this embodiment, the endoscope is not limited to be a fiber scope but may be an electronic scope or the like provided with a solid state imaging device as an imaging means and is not limited to be a flexible endoscope but may be a rigid endoscope.

Figure 34:
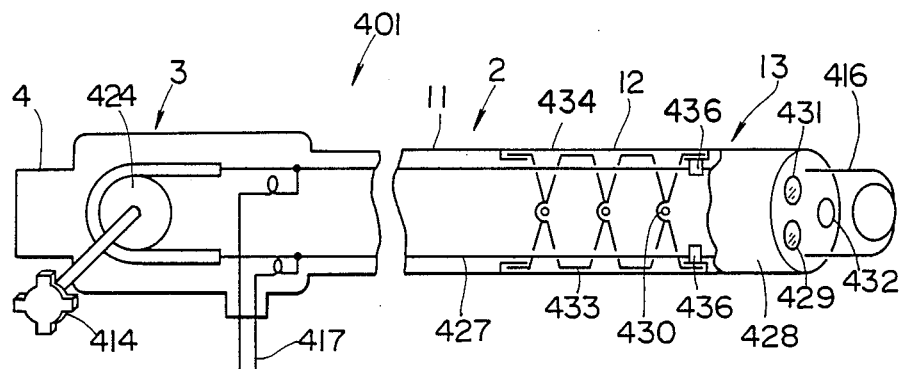
FIGS. 34 and 35 relate to the eighth embodiment of the present invention.
Figure 35:
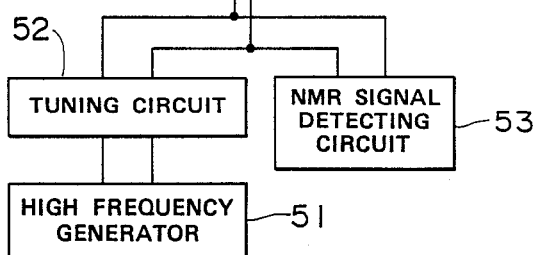
Figure 35:
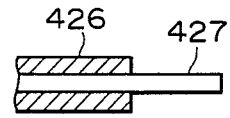

FIGS. 34 and 35 show the eighth embodiment of the present invention.

In an endoscope 401 of this embodiment, the tip part 13 is provided with a substantially columnar tip part body 428 made of such rigid material as a metal.

Such objective lens system 429 as can form an observed image on the entrance end surface of an image guide not illustrated transmitting the observed image to the eyepiece part 4, a light distributing lens 431 which can feed an illuminating light from the light source apparatus 7 to an observed position through a light guide not illustrated and a forceps channel 432 through which a treating tool or the like can be inserted are provided on the front end surface of the above mentioned tip part body 428.

The foremost articulating frame 433 of a plurality of articulating frames 433 forming the curvable part 12 and rotatably connected in the lengthwise direction by pivoting parts 430 is externally fitted to the rear end of the above mentioned tip part body 428 and the articulating frames are coated on the outer peripheral surface with a flexible tube 434 forming the outer fitting of the insertable part 2.

A curving operation knob 414 provided on the operating part 3 can rotate a pulley 424 arranged within the operating part 3. An angle wire 427 formed of such material as a metal and able to curve the tip part 13, for example, vertically is wound on this pulley 424. By the way, the angle wire is coated with an insulating member 426 as shown in FIG. 35 in the part to be in contact with the pulley 424.

The above mentioned angle wire 427 is inserted at both ends through wire receptacles not illustrated provided within the insertable part 2 from within the operating part 3, is fixed to a tip part body 428 by fixing parts 436 provided on the inner periphery of the tip part body 428, is further passed through the front end surface of the tip part body 428 and is connected to an NMR metering antenna 416 to form a signal line.

The above mentioned NMR metering antenna 16 is coated with an insulating member and is formed to be like a single winding loop of an outside diameter substantially equal to or somewhat smaller than the outside diameter of the tip part body 428.

The above mentioned angle wire 427 is connected to signal cables 417 within the operating part 3. These signal cables 317 are relaxed so as to be able to absorb the displacement even if the angle wire 427 reciprocates to curve the curvable part 12, are extended together with a light guide not illustrated out of the operating part 3, are inserted through the universal cord 5 and are connected to the tuning circuit 52 and NMR signal detecting circuit 53 provided within the light source apparatus 7. The above mentioned tuning circuit 52 is connected to the output end of the high frequency generator 51.

The NMR metering means including the above mentioned antenna 416 is the same as is shown in FIG. 5.

The other formations are substantially the same as in the first embodiment.

The operation of this embodiment formed as in the above shall be explained in the following.

As shown in FIG. 2, the examinee 16 is mounted on the bed and a static magnetic field is given to the examinee 16 by the NMR apparatus 17. In this state, the insertable part 2 of the endoscope 40 provided with the NMR metering antenna 416 is inserted through the mouth cavity or the like of the examinee 16, an illuminating light is fed to the light guide not illustrated of the endoscope 401 and the upper layer part or the like of the stomach wall is observed with the observing optical system consisting of the objective lens system 429, image guide not illustrated and eyepiece part 4. For example, in case an abnormal position is discovered in the upper layer part of the stomach wall, the curving operation knob 414 provided on the operating part 3 is operated to push the NMR metering antenna 416 provided in the tip part 13 against the abnormal position. In this state, a high frequency will be delivered to the above mentioned antenna through the high frequency generator 51, tuning circuit 52 and condenser box 33 and a high frequency magnetic field will be output to the abnormal position from this antenna 416. By the way, it is desirable that the direction of this high frequency magnetic field intersects at right angles with the direction of the static magnetic field. When the NMR signal from the abnormal position is received by the above mentioned antenna 416 and is metered by the NMR signal detecting circuit 53, the physiological variation of the abnormal position, for example, whether it is a cancer or not will be able to be detected.

By the way, the pulley 424 may bee made a chain sprocket, the angle wire 427 in the part coated with the insulating member 426 may be replaced with a roller chain and the connecting part of the angle wire 427 with the roller chain may be insulated.

According to this embodiment, when the angle wire 427 curving the curvable part is made to have functions of the signal lines of outputting a high frequency magnetic field from the high frequency generator 51 to the antenna 416 and transmitting the NMR signal from the abnormal position to the NMR signal detecting circuit 53, the signal lines will not be required to be separately inserted through the insertable part 2 and therefore the insertable part 2 of the endoscope 401 provided with the NMR metering antenna in the tip part 13 will be able to be made smaller in the diameter.

Figure 36:
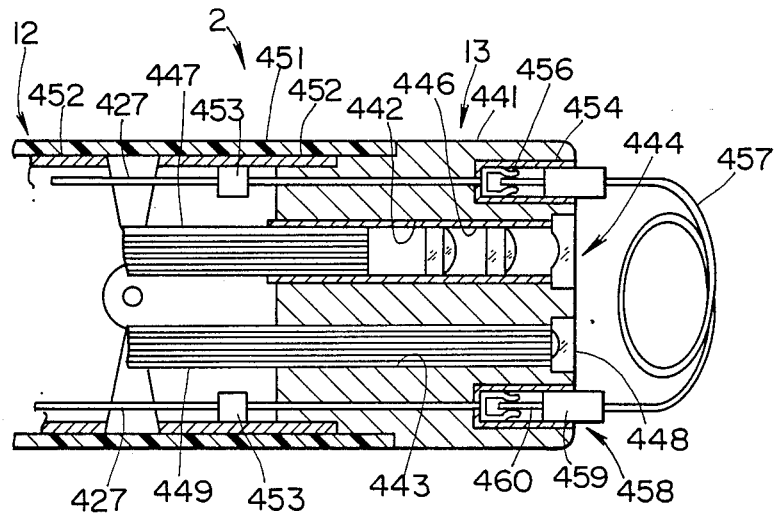
FIG. 36 is a sectioned view of the tip part of the insertable part of an endoscope in the ninth embodiment of the present invention.

FIG. 36 shows the ninth embodiment of the present invention.

The tip part 13 of the endoscope 401 is provided with a substantially columnar tip part body 441 made of such rigid material as a metal. An observing through hole 442, an illuminating through hole 443, an air and water feeding channel through hole not illustrated and a forceps channel through hole not illustrated are provided parallelly with the lengthwise direction of the insertable part 2 in this tip part body 441.

The above mentioned observing through hole 442 is fitted with a cylindrical lens frame 446 in which an objective lens system 444 is internally fitted and fixed. In the rear part of this lens frame 446, the entrance end surface of an image guide 447 is fitted and fixed in the image forming position of the objective lens system 444 so that an observed image may be transmitted to the eyepiece part 4 provided in the operating part 3. A light distributing lens 448 is fitted at the front end of the illuminating through hole 443 so that the illuminating light may be fed into the body cavity by a light guide 449 provided on the rear end surface of the light distributing lens 448.

The above mentioned air and water feeding channel not illustrated and forceps channel not illustrated are connected respectively with channel tubes to form an air and water feeding channel and forceps channel.

The foremost articulating frame 452 of a plurality of articulating frames 452 coated with a tube 451 as a sheath is externally fitted and fixed on the outer periphery of the rear part of the above mentioned tip part body 441. Angle wire 427 inserted through the insertable part 2 and curving the curvable part 12, for example, vertically are fixed by fixing parts 453 on the inner peripheral surface of this foremost articulating frame 452, are further passed through the tip part body 441 and are connected to pawl-like contacts 456 provided within connecting member 454 which are formed to be cylindrical of an elastic material and are fitted and fixed in the tip part body 441 so that their centers may be parallel with the lengthwise direction of the insertable part 2.

Terminals 458 provided at both ends of an NMR metering antenna formed to be like a single winding loop of an outside diameter substantially equal to or somewhat smaller than the outside diameter of the above mentioned tip part body 441 and coated with an insulating member are removably inserted respectively into the above mentioned connecting members 454. In this terminal 458, a cylindrical water-tight part 459 presses the inner peripheral surface of the connecting member 454 to keep water-tightness and a pin-like contact 460 provided on the rear end surface of this water-tight part 459 connects with the above mentioned pawl-like contact 456 which is thus electrically connected with the NMR metering antenna 457.

According to this embodiment, as the NMR metering antenna 457 is removably fitted, in case, with this endoscope 401, NMR is not metered but only the interior of the body cavity is observed, when the antenna 457 is removed and a blind plug or the like is inserted and fitted in each connecting member 454, a favorable visual field will be able to be obtained.

The other formations, metering means, operations and effects are the same as in the eighth embodiment.

Figure 37:
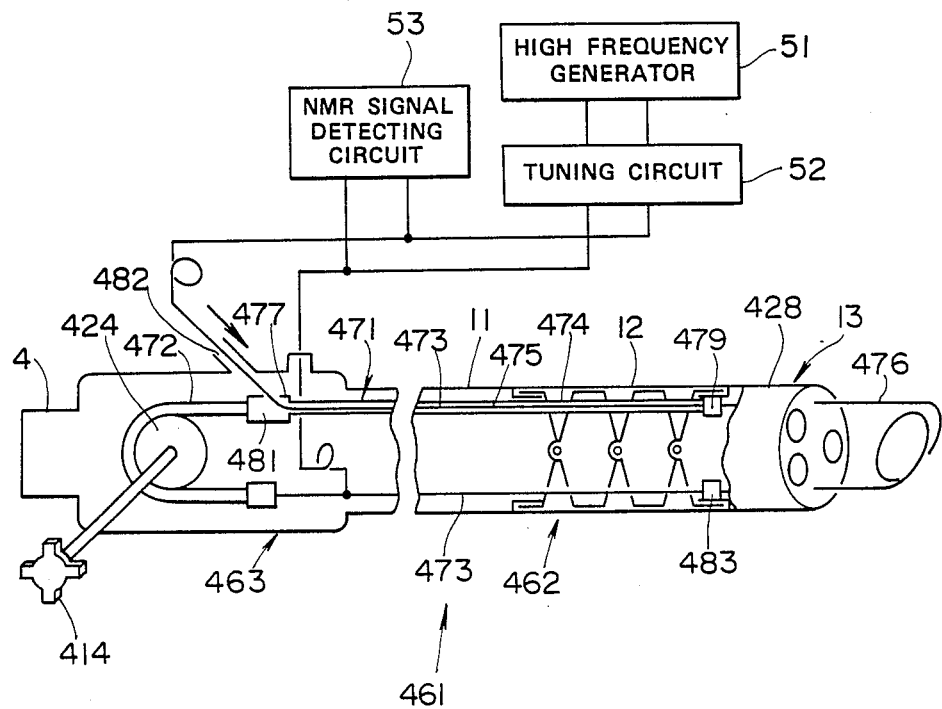
FIG. 37 is an explanatory view showing the formation of an endoscope apparatus in the 10th embodiment of the present invention.

FIG. 37 shows the 10th embodiment of the present invention.

In this embodiment, a curving operation knob 414 provided on the operating part 3 can be rotated by a pulley 424 arranged within the operating part 3. An angle wire 471 which can curve the curvable part 12, for example, vertically is wound on this pulley 424.

The above mentioned angle wire 71 is formed of a winding part 472 to be wound on the above mentioned pulley 424, signal lines 473 which can pull and relax the tip part body 428, a tube member 474 having hollow part inserting the above mentioned signal lines 473 and an NMR metering antenna part 476.

The above mentioned winding part 472 is, for example, an insulative wire or roller chain and is long enough to fully curve the curvable part.

The above mentioned tube member 474 is inserted through the insertable part 2, is flexible, has a leading inlet path 475 as a hollow part for the signal lines 473 formed within, is connected at one end to one end of the above mentioned winding part through a connecting member 477 and is fixed at the other end by a fixing part 479 provided on the inner periphery of the rear part of the tip part body 428.

The above mentioned connecting member 477 has a hole 481, for example, cylindrical, communicating with the above mentioned leading inlet path 475 and passing through the outer periphery of the connecting member 477. The fixing part 479 has a hole not illustrated communicating with the leading inlet path 475, passing through in the tip direction and having the signal line 473 inserted through it.

The above mentioned signal line 473 is led to the leading inlet path 475 through the hole 481 provided in the above mentioned connecting member 477 from an inserting part 482 provided in the side part of the above mentioned operating part 3. The signal line 473 passed through this leading inlet path 475 and inserted through the fixing part 479 passes through the tip part body 428 and forms the NMR metering antenna part 476.

The above mentioned winding part 472 is connected at the other end to the above mentioned antenna part 476 through the signal line 473 passed through the tip part body 428 and is further fixed to a fixing part 483 provided on the inner periphery of the rear part of the tip part body 428.

By the way, such water-tight member not illustrated as, for example, an O-ring through which the signal line 473 is slidable and which can keep water-tightness is inserted and fitted in the position in which the signal line 473 on the above mentioned tube member 474 side passes through the tip part body 428.

· The above mentioned NMR metering antenna part 476 is coated with an insulating member and is formed to be like a single winding loop of an outside diameter equal to or somewhat smaller than the outside diameter of the tip part body 428.

The above mentioned signal line 473 is extended at both ends out of the operating part 3 as relaxed so as to be able to absorb the displacement of the angle wire 471 and is connected, for example, together with a light guide not illustrated to the NMR signal detecting circuit 53 and tuning circuit 52 contained in the light source apparatus not illustrated. The above mentioned tuning circuit 52 is connected to the output end of the high frequency generator 51.

In this embodiment, when the signal line 473 inserted through the tube member 74 and extended out of the operating part 3 is pushed in the direction indicated by the arrow in the drawing, the NMR metering antenna part 476 provided forward of the tip part body 428 will be able to be inclined and, when it used together with the curving operation knob 418, the antenna part 476 will be able to be closely contacted with an abnormal position of a more complicated form and NMR will be able to be metered.

By the way, in this embodiment, only the signal line 473 on one side is inserted through the tube member 474 but the signal lines 473 on both sides may be inserted respectively through the tube members 474 so as to incline the antenna part 476 in two directions and further the antenna part 476 may be made movable forward and rearward.

The other formations, metering means, operations and effects are the same as in the eighth embodiment.

As explained above, according to the eighth to tenth embodiment, there are effects that the insertable part of the endoscope apparatus provided with the NMR metering antenna in the tip part can be made smaller in the outside diameter and the pain of the patient can be reduced.

By the way, in the eighth to tenth embodiments, the endoscope is no limited to be a fiber scope but may be an electronic scope or the like provided with a solid state imaging devices as an imaging means as in the second embodiment and is not limited to be a flexible endoscope but may be a rigid endoscope.

Figure 38:
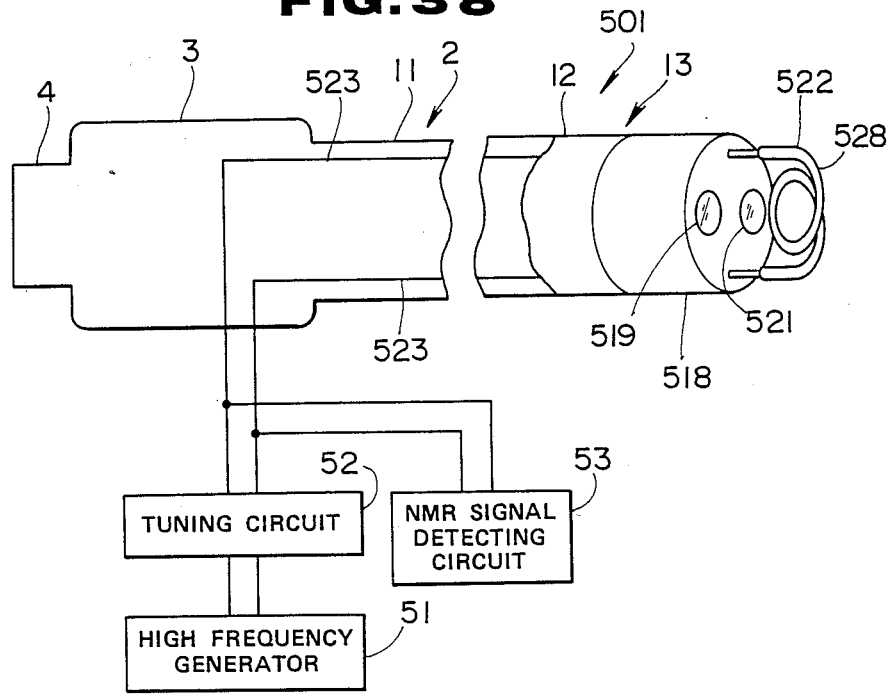
FIG. 38 is an explanatory view showing the formation of an endoscope apparatus in the 11th embodiment of the present invention.

FIG. 38 shows the 11th embodiment of the present invention.

In an endoscope 501 of this embodiment, the tip part 13 is provided with a substantially columnar tip part body 518 made of such rigid material as a metal.

Such objective lens system 519 as can form an observed image on the entrance end surface of an image guide not illustrated transmitting the observed image to the eyepiece part 4 and a light distributing lens system 521 which can feed an illuminating light from the light source apparatus 7 to the observed position through a light guide not illustrated are provided on the front end surface of the above mentioned tip part body 518.

Further, an NMR metering antenna 522 is provided forward of the tip part body 518. Signal lines 523 connected to both ends of this antenna 522 are inserted through the insertable part 2 and are led to the operating part 3.

The signal lines 523 led to this operating part 3 are extended out of the operating part 3, are inserted through the universal cord 5 and are connected to the tuning circuit 52 and NMR signal detecting circuit 53 provided within the light source apparatus 7. The above mentioned tuning circuit 52 is connected to the output end of the high frequency generator 51.

The above mentioned NMR metering antenna 522 is coated with an impregnated member 528 as an index setting means impregnated, for example, with a coloring material and is formed to be like a single winding loop of an outside diameter substantially equal to or somewhat smaller than the outside diameter of the tip part body 518.

The NMR metering means including the above mentioned antenna 522 is the same as is shown in FIG. 5.

The other formations are substantially the same as in the first embodiment.

The operation of this embodiment formed as in the above shall be explained in the following.

As in FIG. 2, the examinee 16 is mounted on the bed 15 and a static magnetic field is given to the examinee 16 by the NMR apparatus 17. In this state, the insertable part 2 of the endoscope 501 provided with the NMR metering antenna 522 is inserted through the mouth cavity or the like of the examinee 16, an illuminating light is fed to a light guide not illustrated of the endoscope 501 and the upper layer part or the like of the stomach wall is observed with the observing optical system consisting of the objective lens system 519, image guide not illustrated and eyepiece part 4. For example, in case an abnormal position is discovered in the upper layer part of the stomach wall, the curving operation knob provided on the operating part 3 is operated to push the NMR metering antenna 522 provided in the tip part 13 against the abnormal position. In this state, a high frequency will be delivered to the above mentioned antenna 522 through the high frequency generator 51, tuning circuit 52 and condenser box 33 and a high frequency magnetic field will be output to the abnormal position from this antenna 522. By the way, it is desirable that the direction of this high frequency magnetic field intersects at right angles with the direction of the static magnetic field. When the NMR signal from the abnormal position is received by the above mentioned antenna 522 and is metered by the NMR detecting circuit 53, the physiological variation of the abnormal position, for example, whether it is a cancer or not will be able to be detected.

When the NMR metering antenna 522 is pushed simultaneously with the above mentioned metering, the coloring material with which the impregnate member 528 is impregnated will be deposited on the abnormal position and will be able to be made an index of the abnormal position. Therefore, even in case, as a result of the examination, for example, a cancer is discovered and a resecting operation is made, as the index of the abnormal position is set, the resecting operation will be able to be smoothly made.

Figure 39:
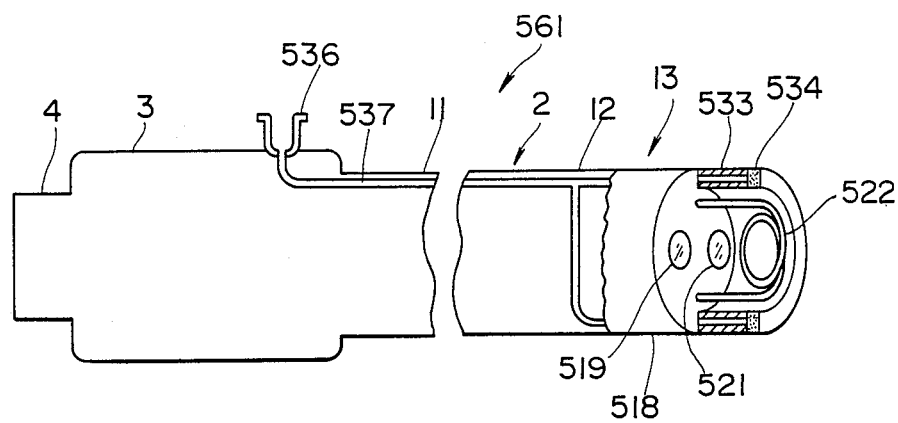
FIG. 39 is an explanatory view showing the formation of an endoscope apparatus in the 12th embodiment of the present invention.

FIG. 39 shows the 12th embodiment of the present invention.

In an endoscope 561 of this embodiment, a flexible cylindrical hood 533 is annularly provided so as to coincide with the outside diameter of the tip part body 518. Further, an impregnated member 534 formed, for example, of a foaming styrol or the like as an index setting means impregnatable with a coloring material is annularly provided on the tip surface of this hood 533.

From a lure mouthpiece 536 provided on the operating part 3, a pipe line 537 is inserted through the insertable part 2, is branched in two directions in the tip part 13, is inserted through the hood 533 and is connected so that a liquid coloring material may be fed.

Within the hood 533 forward of the tip part body 518, an NMR metering antenna 522 is provided and is formed to be like a single winding loop of an outside diameter somewhat smaller than the outside diameter of the tip part body 518.

By the way, the hood 533 may not be cylindrical and may be provided to enclose the antenna 522.

According to this embodiment, as the coloring material can be fed from the lure mouthpiece 536 provided on the operating part 3, the coloring material can be fed only in the case of setting an index and the index can be selectively set.

The other formations, operations and effects are the same as in the 11th embodiment.

Figure 40:
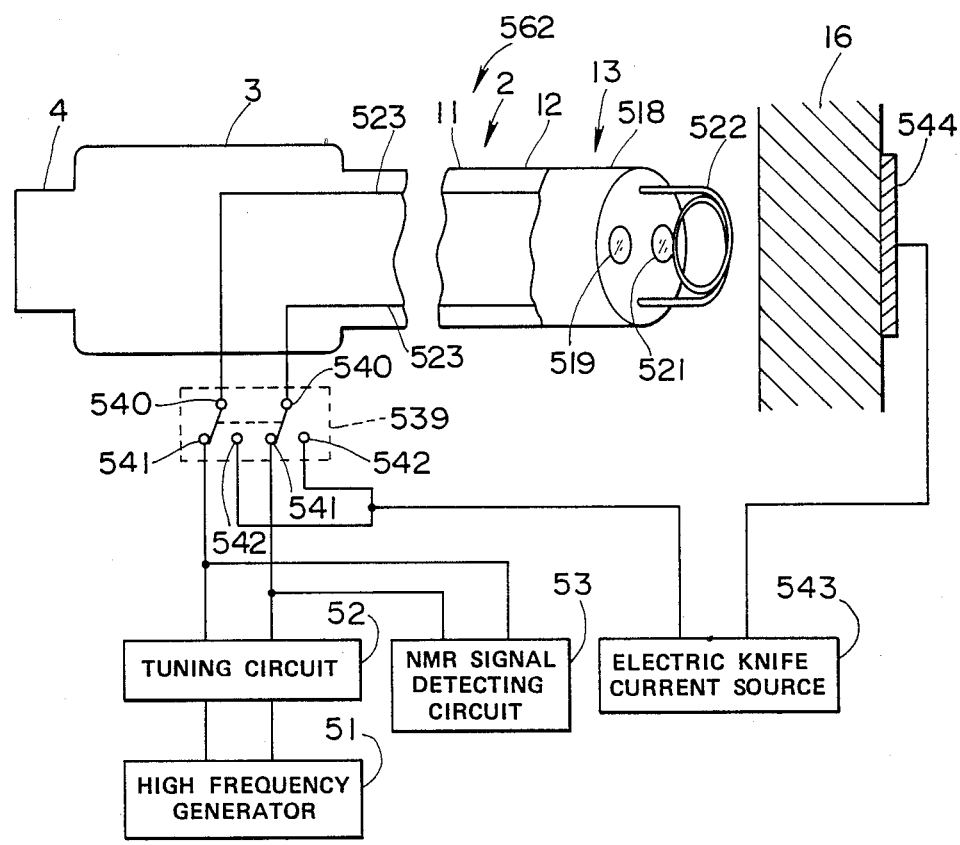
FIG. 40 is an explanatory view showing the formation of an endoscope apparatus in the 13th embodiment of the present invention.

FIG. 40 shows the 13th embodiment of the present invention.

In an endoscope 562 of this embodiment, forward of the tip part body 518, an NMR metering antenna 522 formed to be like a single winding loop of an outside diameter equal to or somewhat smaller than the outside diameter of the tip part body 518 is provided and signal lines 523 connected to both ends of the antenna 522 are inserted through the insertable part 2 and are led to the operating part 3.

The signal lines 523 led to the operating part 3 are extended out of the operating part 3 and are connected to contacts 540 of a switching switch 539. One contact 541 of this switching switch 539 is connected to the tuning circuit 52 and NMR signal detecting circuit 53. Also, the other contact 542 of the switching switch 539 is connected to one terminal of an electric knife current source 543 which can feed a high frequency current for an electric knife.

The other terminal of the above mentioned electric knife current source 543 is connected to a polar plate 544 provided on the body surface of the examinee 16.

The operation of this embodiment formed as in the above shall be explained in the following.

Before the endoscope 562 is inserted, the contacts 540 and 541 of the switching switch 539 are made conductive. Then, the insertable part 2 of the endoscope 562 provided with the NMR metering antenna 522 is inserted into the body cavity and the stomach wall upper layer part or the like is observed. For example, in case an abnormal position is discovered in the stomach wall upper layer part, the NMR metering antenna 522 is pushed against the abnormal position. In this state, a high frequency will be delivered to the above mentioned antenna 522 and a high frequency magnetic field will be output to the abnormal position form this antenna 522. When the NMR signal from the abnormal position is received by the above mentioned antenna and is metered by the NMR signal detecting circuit 53, the physiological variation cf the abnormal position, for example, whether it is a cancer or not will be able to be detected. Here, in case a cancer or the like is discovered, while the NMR metering antenna 522 is pushed, the switching switch 539 will the high frequency current from the electric knife current source 543 will flow between the antenna 522 and abnormal position, the abnormal position will be able to be cauterized, the index will be able to be set and the abnormal position will be able to be recognized at the time of the resecting operation.

According to this embodiment, as the object can be cauterized by switching the switching switch 539 only in case it is necessary to do so, the index can be selectively set.

Figure 41:
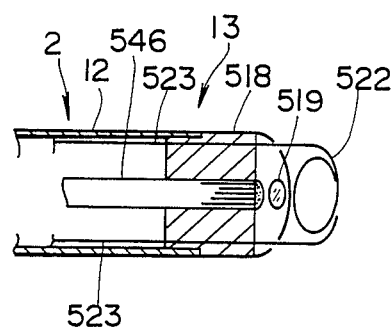
FIG. 41 is an explanatory view of the tip part of the insertable part of an endoscope in the 14th embodiment of the present invention.

FIG. 41 shows the 14th embodiment of the present invention.

In the endoscope of this embodiment, in the center part of the tip part body 518, a laser light guide 546 as an index setting means which can transmit a laser light emitted from a laser apparatus not illustrated is provided as inserted through the insertable part 2 and the exit end surface of this light guide 546 coincides with the tip surface of the tip part body 518.

An NMR metering antenna 522 formed to be like a single winding loop of an outside diameter substantially equal to or somewhat smaller than the outside diameter of the tip part body 518 is provided forward of the above mentioned tip part body 518 and is connected at both ends with signal lines 523 inserted through the insertable part 2.

In this embodiment, by selectively operating the laser apparatus, the abnormal position can be cauterized with the radiation of a laser light, the index can be thereby provided and the abnormal position can be recognized at the time of the resecting operation.

The other formations, operations and effects are the same as in the 11th embodiment.

Figure 42:
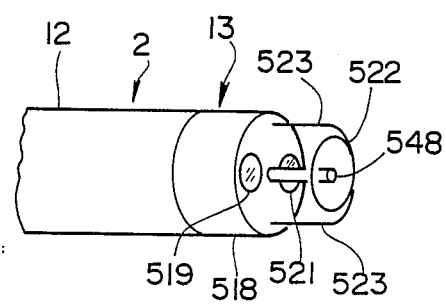
FIG. 42 is an explanatory view of the tip part of the insertable part of an endoscope in the 15th embodiment of the present invention.

FIG. 42 shows the 15th embodiment of the present invention.

In this embodiment, in the center part of the tip part body 518, a light conducting member 584 as an index setting means of a small diameter formed of such material as, for example, ceramics projects forward. This light conducting member 548 can conduct forward a laser light emitted from a semiconductor laser or the like not illustrated provided, for example, within the tip part body 518 so that, in case the NMR metering antenna 522 is pushed against an abnormal position, the tip part of the light conducting member 548 will be able to contact and cauterize the abnormal position.

In this embodiment, an index by which the measuring position of the NMR metering antenna 522 can be recognized by cauterizing with a selectively radiated laser light can be provided and the abnormal position can be recognized at the time of the resecting operation. Further, a tumor can be warmed by controlling the heating amount.

The other formations, operations and effects are the same as in the 11th embodiment.

Figure 43:
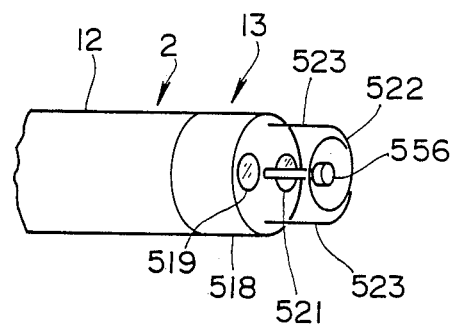
FIG. 43 is an explanatory view of the tip part of the insertable part of an endoscope in the 16th embodiment of the present invention.

FIG. 43 shows the 16th embodiment of the present invention.

In this embodiment, in the center part of the tip part body 518, a cauterizing probe 556 of a small diameter projects forward. Within the tip of this cauterizing probe 556, a heating device not illustrated as such index setting means, for example, as a Zener diode is provided as connected to a current source box not illustrated so that, in case an NMR metering antenna 522 is pushed against an abnormal position, the tip surface of the cauterizing probe 556 will also contact the abnormal position.

In this embodiment, an index by which the measuring position of the NMR metering antenna 522 can be recognized by heating and cauterizing by selectively passing electricity through the heating device can be provided and the abnormal position can be recognized at the time of the resecting operation. Further, a tumor can be warmed by controlling the heating amount.

The other formations, operations and effects are the same as in the 11th embodiment.

Figure 44:
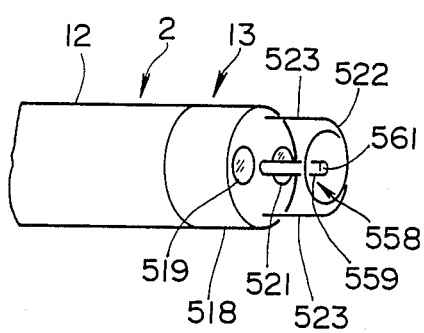
FIG. 44 is an explanatory view of the tip part of the insertable part of an endoscope in the 17th embodiment of the present invention.

FIG. 44 shows the 17th embodiment of the present invention.

In this embodiment, in the center part of the tip part body 518, a cauterizing probe 558 as an index setting means of a small diameter projects forward. This cauterizing probe 558 is formed of a tubular earthing electrode 559 and a rod-like center electrode 561 projecting inward more than the earthing electrode 559 and provided as insulated from the earthing electrode 559. These earthing electrode 559 and center electrode 561 are connected with a microwave generating circuit so that, in case the NMR metering antenna 522 is pushed against an abnormal position, the tip parts of the earthing electrode 559 and center electrode 61 will contact the abnormal position.

In this embodiment, an index by which the measuring position of the NMR metering antenna 522 can be recognized by heating and cauterizing by outputting microwaves to the cauterizing probe 558 can be selectively provided and the abnormal position can be recognized at the time of the resecting operation. Further, a tumor can be warmed by controlling the heating amount.

The other formations, operations and effects are the same as in the 11th embodiment.

As explained above, according to the 11th to 17th embodiments, there are effects that the index representing the measuring position in the case of measuring the body cavity interior with the NMR metering antenna can be easily set and then, at the time of the resecting operation, the affected part can be smoothly treated and cured by confirming the index.

Figure 45:
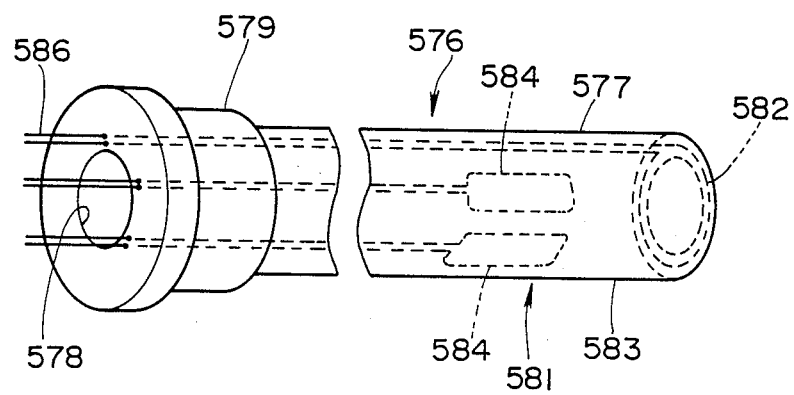
FIG. 45 is a perspective view showing a sliding tube in the 18th embodiment of the present invention.

FIG. 45 shows the 18th embodiment of the present invention.

In this embodiment, an NMR metering antenna is provided in a sliding tube for inserting the endoscope into the depths of the large intestine.

A sliding tube 576 through which an endoscope not illustrated can be inserted into the depths of the large intestine is formed of a cylindrical tube body 577 of a small diameter, a holding part 579 of a large diameter connected to the rear part of the tube body 577 and having an inserting part 578 through which the endoscope not illustrated is to be inserted and an NMR metering antenna 581 provided within the above mentioned tube body 577.

The above mentioned NMR metering antenna 581 is formed of loop-like coil 582 embedded as wound concentrically with a the tube body 577 within the tip part of the tube body 577 and, for example, two saddle like coils 584 embedded in a part of the diametral direction within a thick wall part 583 forming the tube body 577. Signal lines 586 are connected to both ends of the loop-like coil 582 and saddle-like coils 584 so as to be able to be inserted through the tube body 577, to output a high frequency to the loop like coil 582 and saddle-like coils 584 and to deliver NMR signals to an NMR metering apparatus not illustrated. The direction of the high frequency magnetic field generated by this loop-like coil 582, that is, the detecting direction is in the front surface in the inserting direction of the sliding tube and the detecting direction of the saddle-like coil 584 can be made the diametral direction of the tube body 577.

According to this embodiment, as the NMR metering antenna 581 is provided in the sliding tube 576 through which the endoscope is to be inserted, in the case of metering NMR in the depths of the large intestine, an NMR endoscope of a large diameter is not required to be inserted and the pain of the patient can be relieved.

By the way, the NMR metering antenna may be provided in a sheath for a rigid endoscope or in an auxiliary inserting tool for a flexible endoscope.

Figure 46:
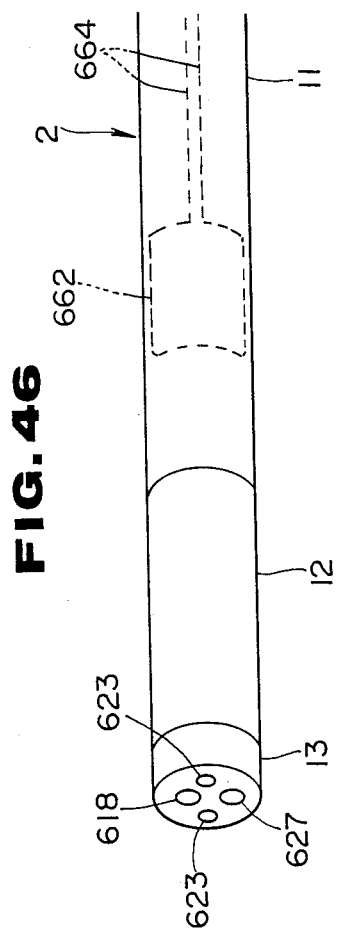
FIGS. 46 to 48 relate to the 19th embodiment of the present invention.
Figure 47:
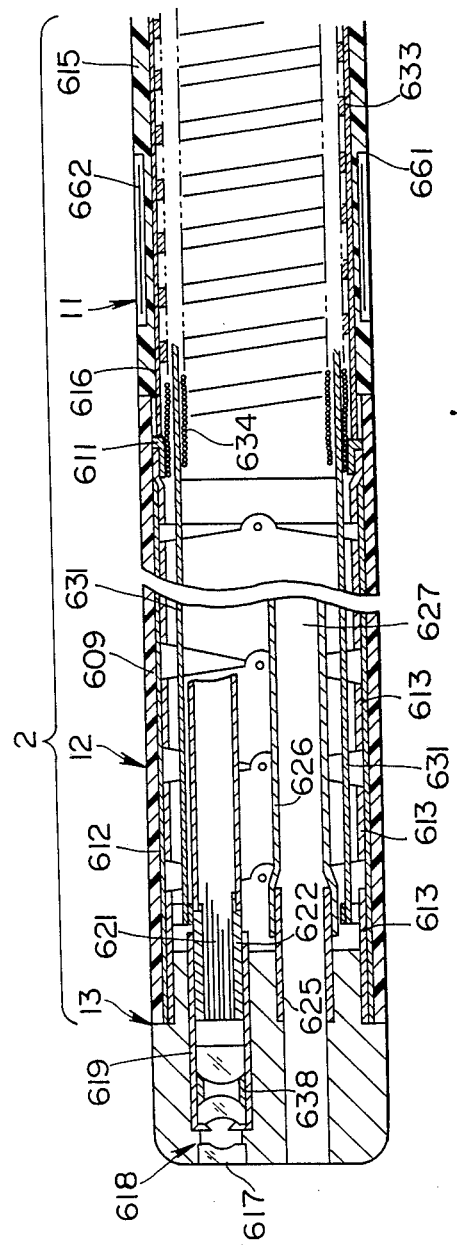
Figure 48:
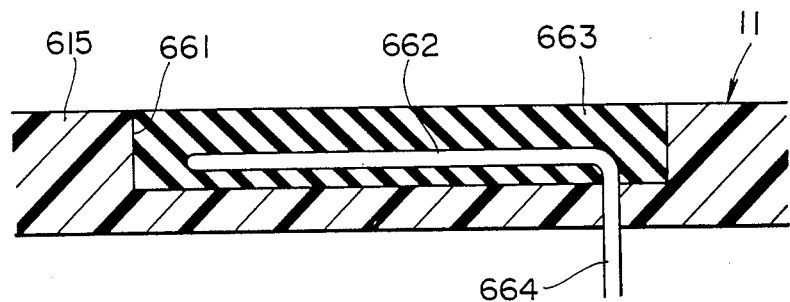

FIG. 46 to 48 show the 19th embodiment of the present invention.

In this embodiment, an NMR metering antenna is provided in the flexible part of the insertable part.

As shown in FIG. 46, the insertable part 2 of the endoscope of this embodiment comprises a tip part 13 formed of a rigid member at the front end, a curvable part 12 formed on the rear side adjacent to this tip part 13 and a flexible part 11 on the rear side adjacent to this curvable part 12.

As shown in FIG. 47, the above mentioned tip part 13 is made smaller in the diameter in the form of steps on the outer periphery near the rear end and an outer cover 609 formed of such flexible material as a synthetic resin is secured at the front end to this tip part 13, covers the curvable part 12, is fitted and secured at the rear end to the outer periphery of a front mouthpiece 611 and is internally fitted inside with a net tube 612. Inside this net tube (also called a blade) 612, substantially ring-like curvable tubes (curvable frames) 613 are connected so as to be alternately rotatable with each other in the direction vertical to the paper surface and in the horizontal direction within the paper surface in FIG. 47. (In FIG. 47, only the case of the side in the direction vertical to the paper surface is shown for the simplification.)

The flexible part 11 adjacent to the outer cover 609 covering the above mentioned curvable part 12 is covered with an outer cover 615 somewhat thicker than this outer cover 609, formed, for example, of a synthetic resin and internally fitted inside with a net tube (blade) 616.

A plurality of through holes parallel with the axial direction of the insertable part 2 are formed in the above mentioned tip part 13. One of the through holes is an observing window 617 fitted with an objective lens system 618 as shown in FIG. 47. A concave lens which is a front lens of this objective lens system 618 is secured directly to the through hole and the rest of this objective lens system 618 is secured to the through hole through a lens frame 619. An image guide 621 formed of a fiber bundle is secured at the front end through a mouthpiece 622 on the rear end of this lens frame 619.

An optical image formed on the front end surface of this image guide 621 by the objective lens system 618 is transmitted by this image guide 621 inserted through the insertable part 2 to the operating part 3 or eyepiece part 4 side on which the image guide 621 is arranged at the other end. The endoscope operator can observe with a naked eye the optical image transmitted through an eyepiece not illustrated by bringing the eye close to the rear end surface of the eyepiece part 4.

As shown in FIG. 46, two through holes are formed on both sides of and adjacently to the observing window 617 of the above mentioned tip part 13, are illuminating windows and are closed with light distributing lenses 623. A light guide not illustrated is secured at the tips to the inner parts of the respective lenses 623. When the light guide inserted through the insertable part 2 and universal cord 5 is connected at the base side end to a light source apparatus not illustrated, the illuminating light of the illuminating lamp will be transmitted, will be emitted from the tip surface, will be expanded by the light distributing lens 623 and will be able to illuminate the object side to have the image formed by the objective lens system 618.

As shown in FIG. 47, in the above mentioned tip part 13, a pipe 625 is secured to the inside of the rear end side of a through hole formed adjacently to a through hole to be an observing window 617, further a flexible tube 626 is fitted a the front end to the outer periphery of the pipe 625 projecting out of the rear end of the through hole and a treating tool channel (or forceps channel) 627 through which a treating tool can be passed is formed within this tube 626. This channel 627 communicates on the base side with a channel leading inlet formed on the side part of the operating part 3.

In the foremost curvable tube 613 of curvable tubes 613 forming the curvable part 12 adjacent to the above mentioned tip part 13, the position opposed through the center of that tube, that is, the part opposed at an angle of 180 degrees is partly incised and is bent to the inside and curving wires 631 are secured as by soldering to this bent part. By the way, in FIG. 47, a pair of wires 631 are inserted in the vertical direction within the paper surface but a pair of wires ar inserted also in the direction vertical to this paper surface.)

The above mentioned pair of wires 631 are inserted through the insertable part 2 and are fitted to a rotary drum not illustrated within the operating part 3 so that, by rotating an angle knob fitted to the rotary shaft of this drum, one of the pair of wires 631 may be pulled but the other may be relaxed to bend the rotatably longitudinally connected curvable tubes 613 horizontally or vertically.

The last step curvable tube 613 of the above mentioned curvable tubes 613 is externally fitted to a small diameter part made steppedly smaller in the diameter in a substantially ring-like front mouthpiece 611 and is secured by a bonding agent or soldering.

This front mouthpiece 611 is steppedly enlarged in the diameter on the rear end side and is fitted with a net tube 616 and a spiral tube (flex) 633 internally fitted inside the net tube 616 at the front ends to be secured.

The respective wires 631 inserted through inside the above mentioned curvable tubes 613 are inserted through a spiral tube 633 connected with the curvable tube 613 in the last step through the front mouthpiece 611.

The wire 631 passed through inside the curvable tubes 613 is further inserted through inside the spiral tube 633 but is inserted through a guide coil 634 on the rear side from the curvable tube 613 part in the last step.

By the way, a diaphragm is formed in the front part of the lens frame 619. The respective lenses fixed in the lens frame 619 are held at a predetermined spacing by a spacer 638.

Now, in this embodiment, as shown in FIGS. 47 and 48, a peripheral groove 661 having a predetermined width in the axial direction is formed on the outer peripheral part of an outer cover 615 of the above mentioned flexible part 11. An NMR metering antenna 662 is contained in this groove 661 further filled with an insulating material.

The above mentioned antenna 662 is wound to be, for example, like a saddle and is arranged on one side of the diametral direction of the flexible part 11. Signal lines 664 are connected to both ends of the above mentioned antenna 662, are led into the flexible part 11 through the above mentioned outer cover 615, net tube 616 and spiral tube 633, are led to the operating part 3 though this flexible part 11, are further inserted through the universal cord 5, are connected to a connector 6 provided at the end of this universal cord 5 and are connected through the above mentioned connector 6 to the tuning circuit 52 and NMR signal detecting circuit 53 provided within the light source apparatus 7.

The other formations are substantially the same as in the first embodiment.

In this embodiment formed as in the above, NMR in the position outside the flexible part 11 of the insertable part 2 can be metered.

According to this embodiment, the NMR metering antenna 662 is made in the form along the contour of the insertable part 2 and can be provided in the flexible part at a high space efficiency. The insertable part can be made smaller in the diameter than in a endoscope containing the antenna in the tip part.

The other operations and effects are the same as in the first embodiment.

Figure 49:
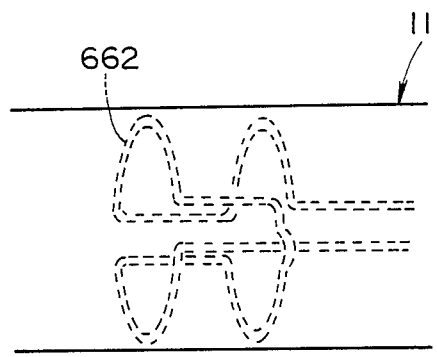
FIG. 49 is an explanatory view showing an antenna shape in the first modification of the 19th embodiment.
Figure 50:
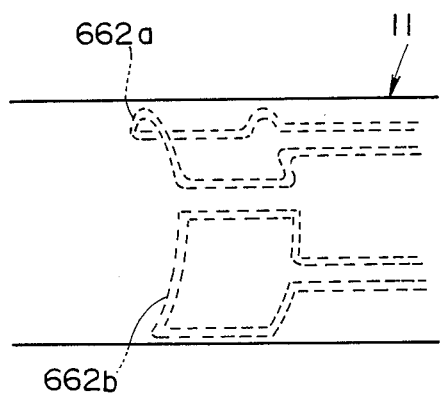
FIG. 50 is an explanatory view showing an antenna shape in the second modification of the 19th embodiment.

FIG. 49 and 50 show a modification of the 19th embodiment.

In the example shown in FIG. 49, an NMR metering antenna 662 is wound to be like saddles on both sides of the diametral direction of the flexible part 11.

According to this embodiment, NMR in the direction intersecting at right angles with the axial direction of the flexible part 11 can be metered and the magnetic field can be made large.

The other formations, operations and effects are the same as in the 19th embodiment.

In the example shown in FIG. 50, a plurality of, for example, two saddle-like antennae 662a and 662b are provided in the peripheral direction of the flexible part 11.

According to this embodiment, by selecting the antenna to be used for metering, the detecting direction can be changed without rotating the insertable part 2.

The other formations, operations and effects are the same a in the 19th embodiment.

By the way, in this embodiment, the shape of the antenna is not limited to be the shapes shown in FIGS. 46, 49 and 50 but may be any various shapes.

Figure 51:
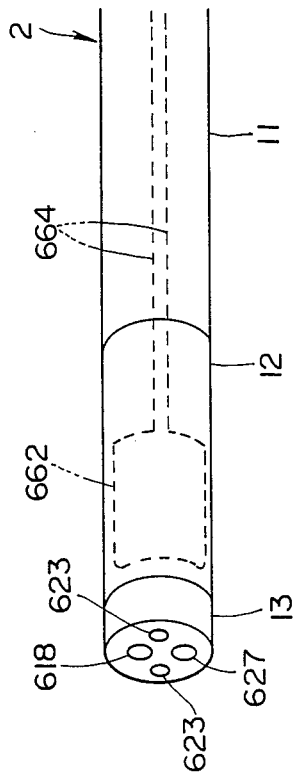
FIGS. 51 and 52 relate to the 20th embodiment of the present invention.
Figure 52:
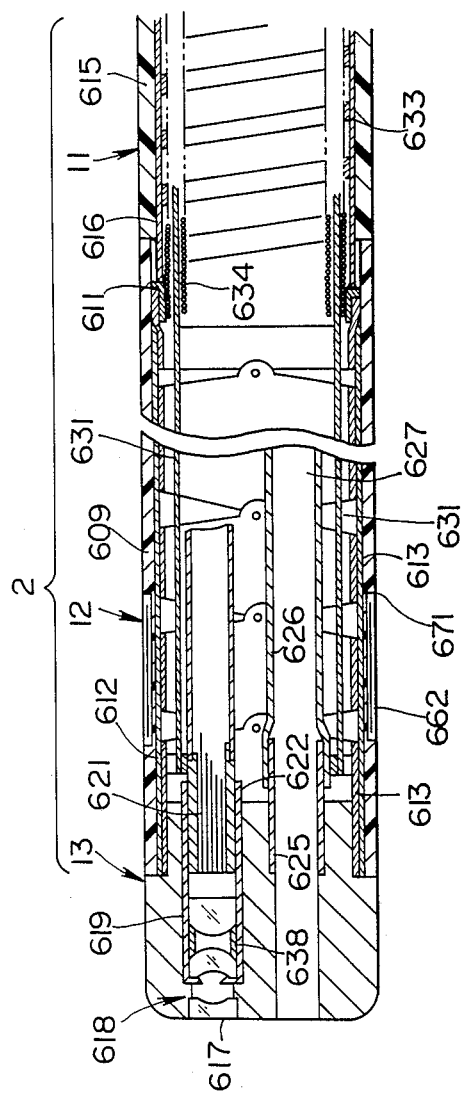

FIGS. 51 and 52 show the 20th embodiment of the present invention.

In this embodiment, an NMR metering antenna is provided in the curvable part of the insertable part.

As shown in FIG. 52, a peripheral groove 671 having a predetermined width in the axial direction is formed on the outer periphery of the outer cover 609 of the curvable part 12. An NMR metering antenna 662 is contained in this groove 671 which is further filled with an insulating material.

The above mentioned antenna 662 is wound to be, for example, like a saddle and is arranged on one side of the diametral direction of the curvable part 12. Signal lines 664 are connected to both ends of the above mentioned antenna 662, are passed through the above mentioned outer cover 609, net tube 612 and curvable tube 613 are led into the curvable part 12 and are led to the operating part 3 through this curvable part 12 and flexible part 11.

The other formations are the same as in the 19th embodiment.

In this embodiment formed as in the above, NMR in the position outside the curvable part 12 of the insertable part 2 can be metered.

According to this embodiment, the NMR metering antenna 662 is made in the form along the contour of the insertable part 2, can be provided in the curvable part 12 at a high space efficiency and can have the insertable part made smaller in the diameter than the endoscope containing the antenna in the tip part.

The other operations and effect are the same as in the first embodiment.

By the way, in this embodiment too, the shape of the antenna 662 can be made such various shapes as are shown in FIGS. 49 and 50.

By the way, in the 19th and 20th embodiments, the NMR metering antenna may be removably fitted to the flexible part 11 or curvable part 12.

The endoscope is not limited to be a fiber scope but may be an electronic scope or the like provided with a solid state imaging device as an imaging means and is not limited to be a flexible endoscope but may be a rigid endoscope.

It is apparent that, in this invention, working modes different in a wide range can be formed on the basis of this invention without deviating from the spirit and scope of the invention. This invention is not restricted by its specific working modes except as limited by the appended claims.

What is claimed is:

1. An NMR metering endoscope apparatus comprising:
   an endoscope body provided with an elongate insertable part having a rear end and a tip part including a tip surface at a front end thereof, an observing window and an illuminating window in the tip part, an observing means for observing an object by receiving light coming from the object entering through said observing window, and an illuminating light outputting means for emitting an illuminating light out of said illuminating window; and
   an NMR metering loop-like antenna fitted to said insertable part tip part by a supporting part so as to be outside the insertable part, said NMR antenna including connecting means for connection to an NMR metering apparatus.

2. An endoscope apparatus according to claim 1 further comprising a hood provided on the tip part of said insertable part and enclosing said tip part, said antenna being fitted to said hood.

3. An endoscope apparatus according to claim 1 further comprising an extensible balloon fitted to the tip part of said insertable part, said antenna being fitted to said balloon.

4. An endoscope apparatus according to claim 1 further comprising a means for changing the direction of orientation of said antenna with respect to said tip part.

5. An endoscope apparatus according to claim 4 wherein said antenna is formed to be bendable and said means for changing the direction of said antenna is a means for bending said antenna.

6. An endoscope apparatus according to claim 4 wherein said antenna is rotatably fitted to the tip part of said insertable part and said means for changing the direction of said antenna is a means for rotating said antenna.

7. An endoscope apparatus according to claim 1 wherein at least one of said antenna and said antenna supporting part has an elasticity so as to positively fix and antenna to a metering position by contacting said antenna with the metering position.

8. An endoscope apparatus according to claim 7 wherein said antenna is spirally wound and has resiliency.

9. An endoscope apparatus according to claim 1 wherein said antenna is removably fitted to the tip part of said insertable part.

10. An endoscope apparatus according to claim 9 further comprising a hood removably provided on the tip part of said insertable part and enclosing said tip part, said antenna being fitted to said hood.

11. An endoscope apparatus according to claim 1 or 9 further comprising a first pipe line fitted to the tip part of said insertable part and becoming loop-like when filled with a fluid, a second pipe line inserted through said insertable part for feeding said fluid to said first pipe line, and supplying means for a conductive fluid with which said first and second pipe lines can be filled, said first pipe line becoming said antenna when filled with said conductive fluid.

12. An endoscope apparatus according to claim 11 wherein said conductive fluid is at least one of a conductive liquid, a conductive gas, a conductive powder, a conductive gel and a mixture of at least two of them.

13. An endoscope apparatus according to claim 1 or 9 further comprising a curvable part which is provided in a predetermined portion of the tip of said insertable part to direct said insertable part tip part in a predetermined direction, an operating means provided in the rear of the rear end of said insertable part and operating to curve said curvable part, a force transmitting member inserted through said insertable part for making said curvable part curvable by the operation of said operating means, and a signal line connected to said antenna inserted through said insertable part and led to the rear end of said insertable part.

14. An endoscope apparatus according to claim 13 wherein at least a part of said force transmitting member and at least a part of said signal line are common to each other.

15. An endoscope apparatus according to claim 13 wherein said force transmitting member has a hollow part though which at least a part of said signal line is inserted.

16. An endoscope apparatus according to claim 1 or 9 further comprising an index forming means forming an index for the metering position of said antenna.

17. An NMR metering endoscope apparatus comprising:
an endoscope body provided with an elongate insertable part having a rear end and a tip part including a tip surface at a front end thereof, an observing window and an illuminating window in the tip part, an observing means for observing an object by receiving light coming from the object entering through said observing window, and an illuminating light outputting means for emitting an illuminating light out of said illuminating window: and
an NMR metering loop-like antenna fitted to said insertable part tip surface, said NMR antenna being formed along the contour of said tip surface and including connecting means for connection to an NMR metering apparatus.

18. An endoscope apparatus according to claim 17 further comprising a tubular member through which said insertable part is inserted and in which said antenna is provided.

19. An endoscope apparatus according to claim 17 wherein said antenna is fitted to an outer cover of said insertable part tip surface.

20. An endoscope apparatus according to claim 19 wherein said insertable part has a curvable part which can direct said insertable part tip part in a predetermined direction and said antenna is fitted to an outer cover of said curvable part.

21. An endoscope apparatus according to claim 1 or 17 further comprising a signal line connected at one end to said antenna, inserted through said insertable part, led to the rear end of said insertable part and connected at the other end to an NMR metering apparatus.

22. An endoscope apparatus according to claim 1 or 17 wherein said observing means further comprises an image forming optical system provided in the tip part of said insertable part, an eyepiece part provided on the rear end of said insertable part and an image transmitting optical system for transmitting to said eyepiece part an object image formed by said image forming optical system.

23. An endoscope apparatus according to claim 1 or 17 wherein said observing means has an image forming optical system provided in the tip part of said insertable part and an imaging means imaging an object image formed by said image forming optical system.

* * * * *